US011687786B2

(12) United States Patent
Andoni et al.

(10) Patent No.: US 11,687,786 B2
(45) Date of Patent: Jun. 27, 2023

(54) PRE-PROCESSING FOR DATA-DRIVEN MODEL CREATION

(71) Applicant: SparkCognition, Inc., Austin, TX (US)

(72) Inventors: Sari Andoni, Austin, TX (US); Keith D. Moore, Cedar Park, TX (US); Syed Mohammad Amir Husain, Georgetown, TX (US)

(73) Assignee: SPARKCOGNITION, INC., Austin, TX (US)

(*) Notice: Subject to any disclaimer, the term of this patent is extended or adjusted under 35 U.S.C. 154(b) by 319 days.

(21) Appl. No.: 17/002,142

(22) Filed: Aug. 25, 2020

(65) Prior Publication Data

US 2020/0387796 A1 Dec. 10, 2020

Related U.S. Application Data

(63) Continuation of application No. 15/582,496, filed on Apr. 28, 2017, now Pat. No. 10,963,790.

(51) Int. Cl.
*G06N 3/08* (2023.01)
*G06N 3/084* (2023.01)
*G06N 3/086* (2023.01)
*G16H 50/70* (2018.01)
*G06N 3/10* (2006.01)
*G06N 3/044* (2023.01)

(52) U.S. Cl.
CPC ............ *G06N 3/084* (2013.01); *G06N 3/086* (2013.01); *G06N 3/105* (2013.01); *G16H 50/70* (2018.01); *G06N 3/044* (2023.01)

(58) Field of Classification Search
None
See application file for complete search history.

(56) References Cited

U.S. PATENT DOCUMENTS

| | | |
|---|---|---|
| 5,692,107 A | 11/1997 | Simoudis et al. |
| 6,058,209 A | 5/2000 | Vaidyanathan et al. |
| 7,092,857 B1 | 8/2006 | Steiner |
| 7,398,260 B2 | 7/2008 | Fiske |
| 7,480,640 B1 | 1/2009 | Elad et al. |
| 8,019,705 B2 | 9/2011 | Fiske |
| 8,150,677 B2 | 4/2012 | Menezes et al. |
| 8,229,734 B2 | 7/2012 | Bennett |

(Continued)

OTHER PUBLICATIONS

An Improved Polynomial Neural Network Classifier Using Real-Coded Genetic Algorithm Chin-Teng Lin; Mukesh Prasad; Amit Saxena IEEE Transactions on Systems, Man, and Cybernetics: Systems Year: 2015, vol. 45, Issue: 11 Pages: 1389-1401, DOI: 10.1109/TSMC.2015.2406855 IEEE Journals & Magazines.

(Continued)

*Primary Examiner* — Alan Chen
(74) *Attorney, Agent, or Firm* — Moore IP Law

(57) ABSTRACT

A method includes receiving input that identifies one or more data sources and determining, based on the input, a machine learning problem type of a plurality of machine learning problem types supported by an automated model building (AMB) engine. The method also includes generating an input data set of the AMB engine based on application of one or more rules to the one or more data sources. The method further includes, based on the input data set and the machine learning problem type, initiating execution of the AMB engine to generate a neural network configured to model at least a portion of the input data set.

20 Claims, 15 Drawing Sheets

(56) References Cited

U.S. PATENT DOCUMENTS

| | | |
|---|---|---|
| 8,233,471 B2 | 7/2012 | Brownrigg et al. |
| 8,256,381 B2 | 9/2012 | Pratt |
| 8,282,557 B2 | 10/2012 | Haynes et al. |
| 8,311,144 B1 | 11/2012 | Sun et al. |
| 8,386,401 B2 | 2/2013 | Virkar et al. |
| 8,505,488 B2 | 8/2013 | Pratt |
| 8,594,222 B1 | 11/2013 | Sun et al. |
| 8,625,496 B2 | 1/2014 | Brownrigg et al. |
| 8,712,942 B2 | 4/2014 | Fiske |
| 8,787,246 B2 | 7/2014 | Brownrigg |
| 8,881,984 B2 | 11/2014 | Santos et al. |
| 8,929,971 B2 | 1/2015 | Haynes et al. |
| 8,982,856 B2 | 3/2015 | Brownrigg |
| 9,292,675 B2 | 3/2016 | Husain |
| 9,578,053 B2 | 2/2017 | Husain et al. |
| 9,646,284 B1 | 5/2017 | Lew et al. |
| 9,785,886 B1 | 10/2017 | Andoni et al. |
| 9,864,928 B2 | 1/2018 | Bober et al. |
| 10,065,717 B1 | 9/2018 | Husain et al. |
| 10,065,718 B1 | 9/2018 | Husain et al. |
| 10,152,687 B2 | 12/2018 | Fotinatos et al. |
| 10,207,816 B1 | 2/2019 | Husain et al. |
| 10,319,476 B1 | 6/2019 | Laborde |
| 10,322,820 B2 | 6/2019 | Husain et al. |
| 10,373,056 B1 | 8/2019 | Andoni et al. |
| 10,402,726 B1 | 9/2019 | Moore et al. |
| 10,410,111 B2 | 9/2019 | Husain |
| 10,410,116 B2 | 9/2019 | Husain et al. |
| 10,410,121 B2 | 9/2019 | Husain |
| 10,635,978 B2 | 4/2020 | Andoni et al. |
| 10,645,736 B2 | 5/2020 | Koshimizu et al. |
| 10,657,447 B1 | 5/2020 | McDonnell et al. |
| 10,733,512 B1 | 8/2020 | Andoni et al. |
| 10,817,781 B2 | 10/2020 | Skiles et al. |
| 2003/0212678 A1 | 11/2003 | Bloom et al. |
| 2005/0234761 A1 | 10/2005 | Pinto et al. |
| 2007/0011114 A1 | 1/2007 | Chen et al. |
| 2009/0326911 A1 | 12/2009 | Menezes et al. |
| 2010/0207721 A1 | 8/2010 | Nakajima et al. |
| 2014/0075570 A1 | 3/2014 | Hsu et al. |
| 2015/0339572 A1 | 11/2015 | Achin et al. |
| 2017/0017903 A1 | 1/2017 | Gray et al. |
| 2017/0220943 A1 | 8/2017 | Duncan et al. |
| 2018/0137424 A1 | 5/2018 | Royval et al. |
| 2018/0300630 A1 | 10/2018 | Andoni et al. |
| 2018/0314938 A1 | 11/2018 | Andoni et al. |
| 2019/0020669 A1 | 1/2019 | Glatfelter et al. |
| 2019/0146479 A1 | 5/2019 | Celia et al. |

OTHER PUBLICATIONS

An Improved Probabilistic Neural Network with GA Optimization Huafen Yang; You Yang, 2012 Fifth International Conference on Intelligent Computation Technology and Automation Year: 2012 pp. 76-79, DOI: 10.1109/ICICTA.2012.26 IEEE Conference Publications.

"Backpropagation vs. Genetic Algorithm for Neural Network Training," printed Mar. 23, 2017, 2pgs.

Character Recogntion System: Performance Comparison of Neural Networks and Genetic Algorithm Md. Shahazan Ali; Md. Nazrul Islam Mondal 2015 International Conference on Computer and Information Engineering (ICCIE) Year: 2015 Pages: 91-94, DOI: 10.1109/CCIE.2015.7399325 IEEE Conference Publications.

"Evolution Strategies as a Scalable Alternative to Reinforcement Learning," Mar. 24, 2017, 2 pgs.

Fiszelew, A. et al., "Automatic Generation of Neural Networks based on Genetic Algorithms," 2003, 7 pgs.

Floreano, Dario et al., "Neuroevolution: from architectures to learning," Review Article, 2008, Evol. Intel. Springer-Verlag, pp. 47-62.

Morse, Gregory et al., "Simple Evolutionary Optimization Can Rival Stochastic Gradient Descent in Neural Networks," GECCO '16, Proceedings of the Genetic and Evolutionary Computation Conference 2016, 8 pgs.

Neural network designs with genetic learning for control of a single link flexible manipulator Sandeep Jain; Pei-Yuan Peng; A. Tzes; F. Khorrami American Control Conference, 1994 Year: 1994, vol. 3 Pages: 2570-2574 vol. 3, DOI: 10.1109/ACC.1994.735023 IEEE Conference Publications.

New adaptive genetic algorithm based on ranking Zhiming Liu; Jiliu Zhou; Su Lai, Proceedings of the 2003 International Conference on Machine Learning and Cybernetics (I EEE Cat. No. 03EX693) Year: 2003, vol. 3 Pages: 1841-1844 vol. 3, DOI: 10.1109/ICMLC.2003.1259796 IEEE Conference Publications.

Pan, Zhengjun et al., "Evolving Both the Topology and Weights of Neural Networks," Parallel Algorithms and Applications, 1996, vol. 9, 7 pgs.

Parker, Matt et al., "Lamarckian Neuroevolution for Visual Control in the Quake II Environment," Proceedings of the 2009 IEEE Congress on Evolutionary Computation, 2009, IEEE, Piscataway, NJ, pp. 2630-2637.

Salimans, Tim et al., "Evolution Strategies as a Scalable Alternative to Reinforcement Learning," Cornell University Library, Mar. 10, 2017, arXiv:1703.03864 [stat.ML], 12 pgs.

Simulation research based on a self-adaptive genetic algorithm Jiang Jing; Meng Li-dong; Li Shu-ling; Jiang Lin 201 O IEEE International Conference on Intelligent Computing and Intelligent Systems Year: 2010, vol. 3 Pages: 267-269, DOI: 10.1109/ICICISYS.2010.5658541 IEEE Conference Publications.

Theoretical analysis of evolutionary algorithms with an infinite population size in continuous space. Part I: Basic properties of selection and mutation Xiaofeng Qi; F. Palmieri IEEE Transactions on Neural Networks Year: 1994, vol. 5, Issue: 1 Pages: 102-119, DOI: 10.1109/72.265965 IEEE Journals & Magazines.

Wikipedia—Softmax function, https://en.wikipedia.org/wiki/Softmax_function (Year: 2020).

Wong, G. et al., "Enhancing Competitive Island Cooperative Neuroevolution through Backpropagation for Pattern Classification," International Conference on Neural Information Processing, 2015, 10 pgs.

Zhang, M. et al., "Using Back Propagation Algorithm and Genetic Algorithms to Train and Refine Neural Networks for Object Detection," Database and Expert Systems Applications, DEXA 1999, Lecture Notes in Computer Science, vol. 1677, Springer, Berlin, Heidelberg, 12 pgs.

Stanley, Kenneth O. et al., "Evolving Neural Networks through Augmenting Topologies," Evolutionary Computation, vol. 10(2) 2002, pp. 99-127.

Zhang, Byoung-Tak et al., "Evolving Optimal Neural Networks Using Genetic Algorithms with Occam's Razor," Complex Systems, vol. 7, 1993, pp. 199-220.

Communication pursuant to Article 94(3) EPC for Application No. 18182208.1 dated Apr. 28, 2021, 6 pgs.

Singapore Written Opinion for Application No. 10201805558U dated Jun. 10, 2021, pp. 1-10.

410

Add New Model

[ WDBC Predict ]

Max. Training Time [0] hrs. [15] min.

● Supervised  ○ Unsupervised

Upload Dataset(s)

Drag and drop dataset(s) or browse your files

420

Add New Model

[ WDBC Predict ]

Max. Training Time [0] hrs. [15] min.

● Supervised  ○ Unsupervised

Upload Dataset(s)

*Uploading WDBC.csv...*

430

Add New Model

[ WDBC Predict ]

Max. Training Time [0] hrs. [15] min.

● Supervised  ○ Unsupervised

Identify Goal

[ Predict Target(s) ]
[ Forecast Failures ]

440

Add New Model

[ WDBC Predict ]

Max. Training Time [0] hrs. [15] min.

● Supervised  ○ Unsupervised

Identify Target(s)

[ ID ]
[ Diagnosis ]
[ Mean Radius ]
[ Mean Texture ]

( Start Training )

*FIG. 4*

Add New Model

WDBC Predict

Max. Training Time [0] hrs. [15] min.

◉ Supervised   ○ Unsupervised

Upload Dataset(s)

Drag and drop dataset(s) or browse your files

---

Add New Model

WDBC Predict

Max. Training Time [0] hrs. [15] min.

◉ Supervised   ○ Unsupervised

Upload Dataset(s)

*Uploading WDBC.csv...*

---

Add New Model

WDBC Predict

Max. Training Time [0] hrs. [15] min.

◉ Supervised   ○ Unsupervised

Identify Goal

Predict Target(s)

Forecast Failures

---

Add New Model

WDBC Predict

Max. Training Time [0] hrs. [15] min.

◉ Supervised   ○ Unsupervised

Identify Target(s) — 540

ID

Diagnosis

Mean Radius

Mean Texture

Start Training

*FIG. 5*

| Add New Model | Upload Dataset(s) |
|---|---|
| Windfarm Failure Forecast<br><br>Max. Training Time  3 hrs. 00 min.<br><br>⦿ Supervised    ○ Unsupervised | Drag and drop dataset(s)<br>or browse your files |

| Add New Model | Upload Dataset(s) |
|---|---|
| Windfarm failure forecast<br><br>Max. Training Time  3 hrs. 00 min.<br><br>⦿ Supervised    ○ Unsupervised | *Processing folder "C:\<br>Windfarm data"* |

— 620

| Add New Model | Identify Goal |
|---|---|
| Windfarm failure forecast<br><br>Max. Training Time  3 hrs. 00 min.<br><br>⦿ Supervised    ○ Unsupervised | Predict Target(s)<br>Forecast Failures |

— 630

| Add New Model | Identify Asset Col(s) |
|---|---|
| Windfarm failure forecast<br><br>Max. Training Time  3 hrs. 00 min.<br><br>⦿ Supervised    ○ Unsupervised | *Turbine ID*<br><br>Min. Lead Time  3  days ▼<br><br>Add Failures |

Add New Model — 650

Windfarm failure forecast

Max. Training Time [3] hrs. [00] min.

◉ Supervised   ○ Unsupervised

Add Failures

Asset Name ▼

Start 📅   End 📅

+ Add Another Failure...

[Upload Failures]  [Start Training]

---

Add New Model — 660

Windfarm failure forecast

Max. Training Time [3] hrs. [00] min.

◉ Supervised   ○ Unsupervised

Upload Failures

*Uploading Failures.csv...*

---

Add New Model — 670

Windfarm failure forecast

Max. Training Time [3] hrs. [00] min.

◉ Supervised   ○ Unsupervised

Upload Failures

Asset Name   [ID ▼]

Fail Start   [Fail_Start ▼]

Fail End     [Fail_End ▼]

[Start Training]

*FIG. 6B*

Input set of 200 models at start of epoch N
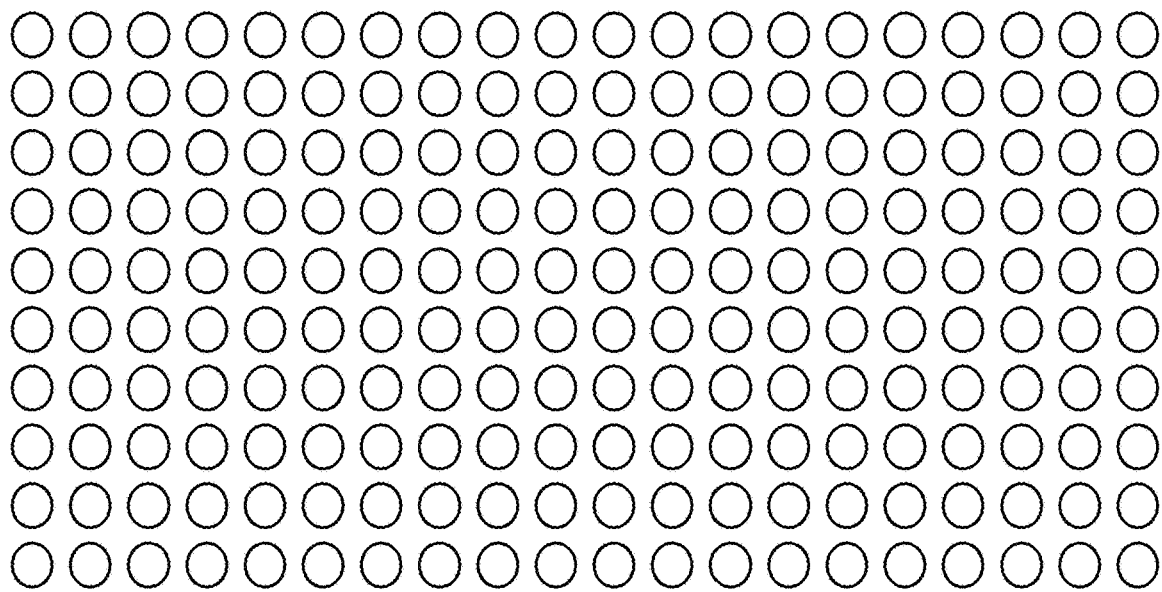
700
750
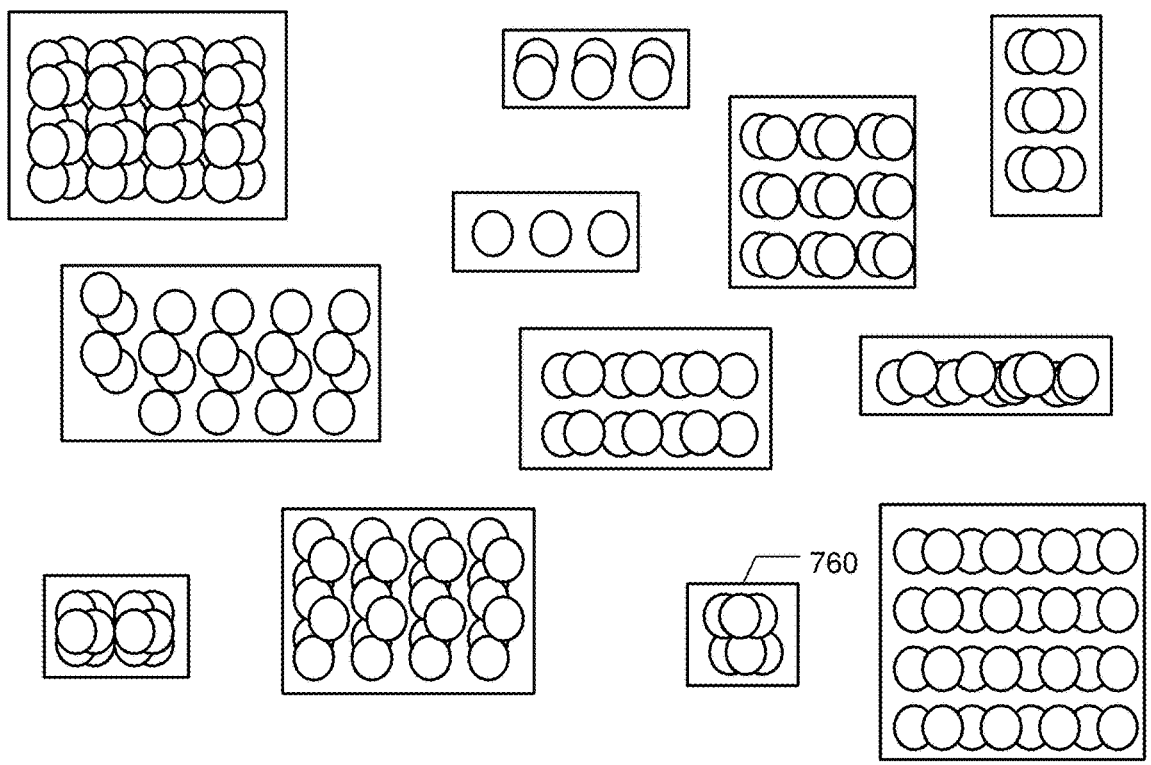
Evaluate model fitness and cluster models into species based on genetic distance
760
FIG. 7

Determine species fitness, identify "elite species," and remove stagnant species
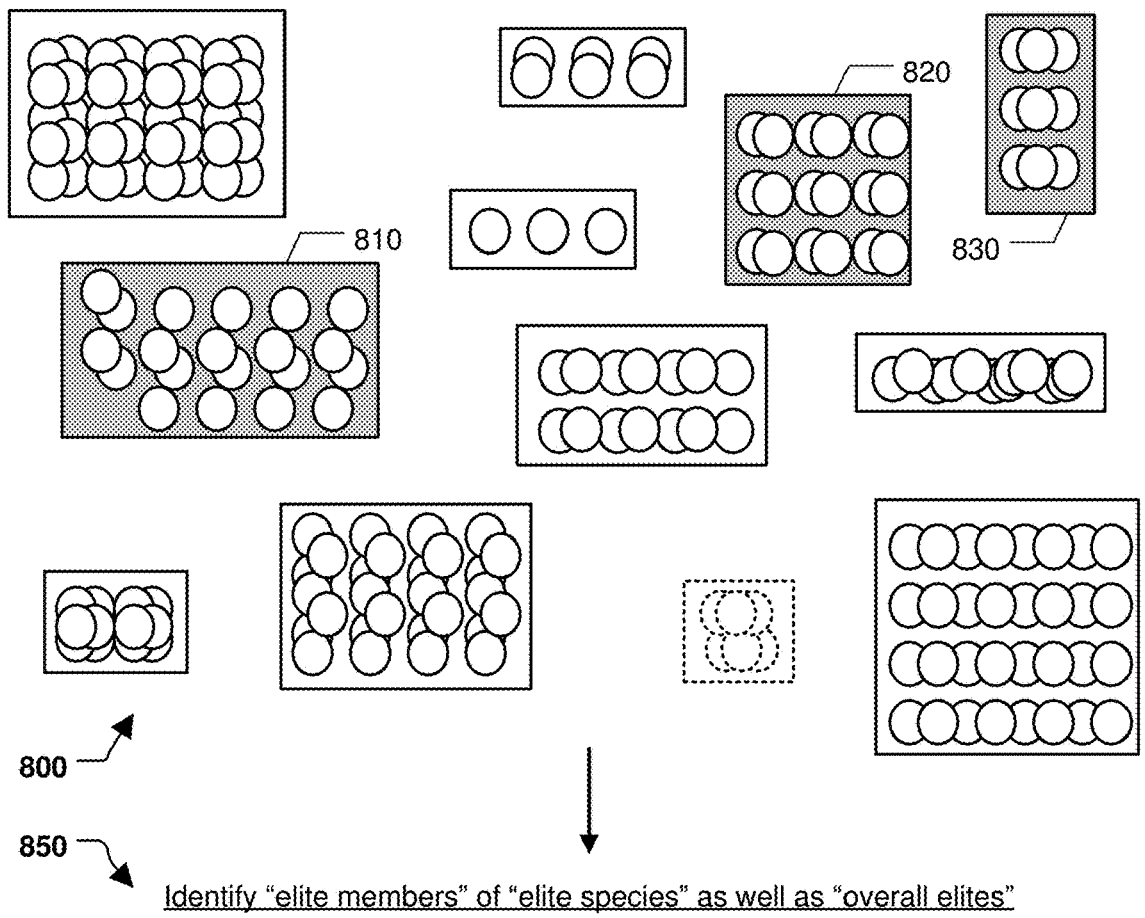
Identify "elite members" of "elite species" as well as "overall elites"
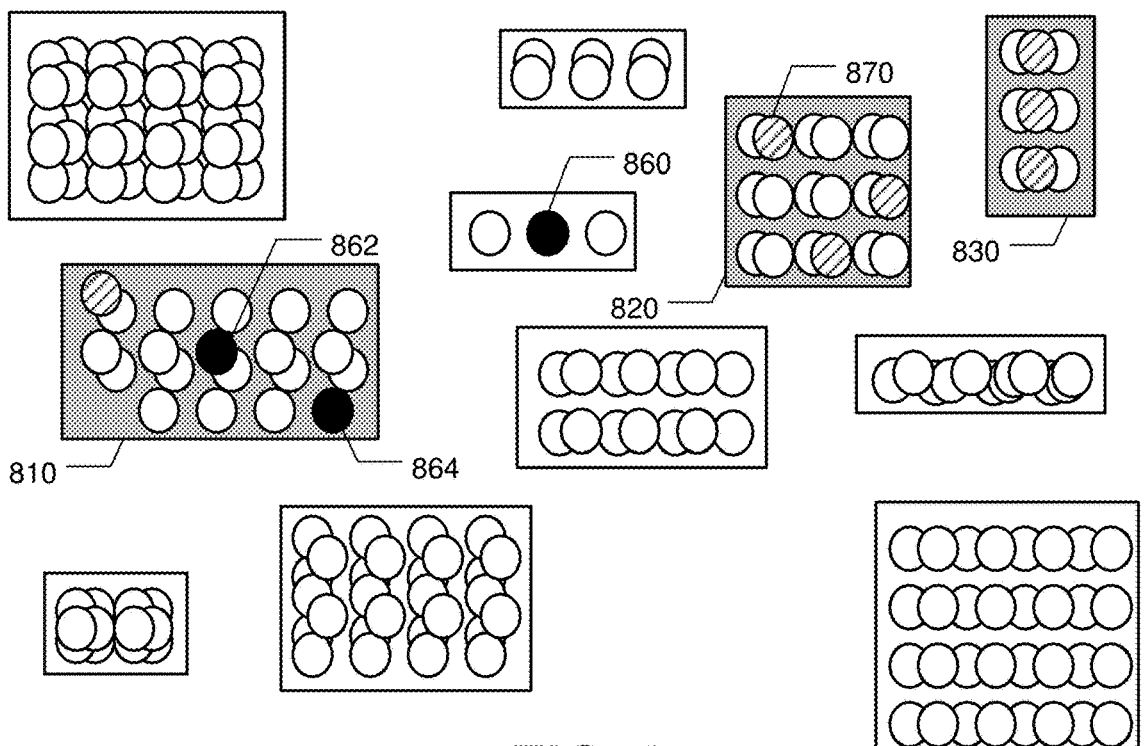
FIG. 8

PRE-PROCESSING FOR DATA-DRIVEN MODEL CREATION

CROSS-REFERENCE TO RELATED APPLICATIONS

The present application claims priority to and is a continuation of U.S. patent application Ser. No. 15/582,496 entitled "PRE-PROCESSING FOR DATA-DRIVEN MODEL CREATION," filed Apr. 28, 2017, the contents of which are incorporated herein by reference in their entirety.

BACKGROUND

Computers are often used to solve complex quantitative and qualitative problems. For problems that involve a large data set, a specially trained professional, known as a data scientist, is often hired. The data scientist interprets the data set and constructs models that can be processed by computers to solve the problem. However, hiring data scientists is cost prohibitive for many organizations.

For certain types of problems, advanced computing techniques, such as genetic algorithms or backpropagation, may be available to develop a model, such as a neural network, that is comparable in accuracy to a model that would be created by a data scientist. However, genetic algorithms may take a large number of iterations to converge on an acceptable neural network, and backpropagation may be slow when a large data set is being modeled or when the neural network includes a large number of nodes, connections, or layers.

Furthermore, various types of machine-learning problems exist. For example, regression problems involve evaluating a series of inputs to predict a numeric output, classification problems involve evaluating a series of inputs to predict a categorical output, and reinforcement learning involves performing actions within an environment to optimize some notion of a positive reward. Due to the differences in the various types of problems, the available mechanisms to generate and train a neural network or other machine learning solution may be problem-specific. Moreover, because solution mechanisms may be problem specific, a data scientist may need to know type of problem to be solved before selecting a solution mechanism. For example, a support vector machine (SVM) may be suitable for some classification problems, logistic regression may be suitable for some regression problems, and a specialized machine learning package, such as TensorFlow, may be suitable for reinforcement learning. Thus, generating and training neural networks that meet performance requirements for each of multiple types of problems faced by an enterprise may be slow and difficult.

SUMMARY

The present application describes a pre-processor that enables data-driven model building for neural networks. In a particular example, the pre-processor may automatically modify data received from one or more data sources and may automatically identify a type of machine learning problem (e.g., regression vs. classification vs. reinforcement learning) for which a neural network is to be generated. The pre-processor generates output that is provided to an automated model building engine. For example, the pre-processor may generate an input data set for the automated model building engine, where the input data set includes training and testing data. In an illustrative aspect, the automated model building engine utilizes a genetic algorithm and selective backpropagation to generate and train a neural network, although it is to be understood that in alternative examples different generation and/or training algorithms may be used. Thus, as used herein an "automated model building engine" may be one or more devices, modules, or components configured to determine at least one machine learning solution (e.g., neural network) that models all or a portion of an input data set. The ability to automatically initialize a model building engine based on provided data sources without a priori knowledge of the type of machine learning problem to be solved enables data-driven model creation for multiple types of problems. For example, neural networks that can be applied for regression, classification, and reinforcement learning problems may be generated by the same automated model building engine based on information determined by the pre-processor. In the example in which the automated model building engine utilizes a genetic algorithm and selective backpropagation, such a combination may enable generating a neural network that models a particular data set with acceptable accuracy and in less time than using genetic algorithms or backpropagation alone.

As an illustrative, non-limiting example, consider a home with four temperature sensors that periodically collect temperature readings in the living room (L), the dining room (D), the master bedroom (M), and the guest bedroom (G), respectively. In this example, a data set may include four columns, where each column corresponds to temperature readings from a particular sensor in a particular room, and where each row corresponds to a particular time at which the four sensors took a temperature reading. It may be of interest to predict the temperature in one of the rooms, e.g., L, given the temperature in the other three rooms, e.g., D, M, and G. A neural network may be suitable for such a problem, where the neural network has D, M, and/or G as input nodes and L as an output node. For example, a neural network that predicts an output value of L with 90% accuracy given input values of D, M, and/or G may be an acceptable solution.

In accordance with the described techniques, a combination of a genetic algorithm and an optimization algorithm such as backpropagation, a derivative free optimizer (DFO), an extreme learning machine (ELM) or similar optimizer may be used to generate and then train a neural network. It is to be understood that characterization of any system components of method steps as "optimizers" or "optimization trainers," and use of such terminology herein, is not to be interpreted as requiring such components or steps to generate optimal results to the extreme (e.g., 100% prediction or classification accuracy). Rather, user of such terms is to be interpreted as indicating an attempt generate an output that is improved in some fashion relative to an input. For example, an optimization trainer that receives a trainable model as input and outputs a trained model may attempt to improve a prediction or classification accuracy of the trainable model by modifying one or more attributes of the trainable model to generate the trained model. Genetic algorithms are iterative adaptive search heuristics inspired by biological natural selection. The genetic algorithm may start with a population of random models that each define a neural network with different topology, weights and activation functions. Over the course of several epochs (also known as generations), the models may be evolved using biology-inspired reproduction operations, such as crossover (e.g., combining characteristics of two neural networks), mutation (e.g., randomly modifying a characteristic of a neural network), stagnation/extinction (e.g., removing neural networks whose accuracy has not improved in several epochs), and selection (e.g., identifying the best performing neural networks via testing). In addition, the best performing models of an epoch may be selected for reproduction to generate a trainable model. The trainable model may be trained using backpropagation to generate a trained model. When the trained model is available, the trained model may be re-inserted into the genetic algorithm for continued evolution. Training a model that is generated by breeding the best performing population members of an epoch may serve to reinforce desired "genetic traits" (e.g., neural network topology, activation functions, connection weights, etc.), and introducing the trained model back into the genetic algorithm may lead the genetic algorithm to converge to an acceptably accurate solution (e.g., neural network) faster, for example because desired "genetic traits" are available for inheritance in later epochs of the genetic algorithm.

A method in accordance with the present disclosure may include receiving, at a processor of a computing device, input that identifies one or more data sources and determining, based on the input, a machine learning problem type of a plurality of machine learning problem types supported by an automated model building (AMB) engine. The method may also include generating an input data set of the AMB engine based on application of one or more rules to the one or more data sources. The method may further include, based on the input data set and the machine learning problem type, initiating execution of the AMB engine to generate a neural network configured to model at least a portion of the input data set.

A computer system in accordance with the present disclosure may include a memory that stores an input data set and a plurality of data structures. For example, each data structure may be a model of a neural network that models the input data set. The computer system may also include at least one processor that is configured to execute a recursive search. For example, the recursive search may be a genetic algorithm to generate a neural network that best models the input data set. During a first iteration of the recursive search, the processor may determine a fitness value for each of the data structures (e.g., neural network models) based on at least a subset of the input data set. The processor may also select a subset of data structures based on their respective fitness values and may perform at least one of a crossover operation or a mutation operation with respect to at least one data structure of the subset to generate a trainable data structure. The processor may further provide the trainable data structure to an optimization trainer that is configured to train the trainable data structure based on a portion of the input data set to generate a trained structure and to provide the trained data structure as input to a second iteration of the recursive search that is subsequent to the first iteration.

BRIEF DESCRIPTION OF THE DRAWINGS

FIGS. 4, 5, 6A, and 6B illustrate particular examples of graphical user interfaces (GUIs) that may receive input used by the pre-processor of FIG. 3 and/or by one or more components of the system of FIG. 1;

FIG. 7 illustrates particular examples of first and second stages of operation at the system of FIG. 1;

FIG. 8 illustrates particular examples of third and fourth stages of operation at the system of FIG. 1;

DETAILED DESCRIPTION

Figure 1:
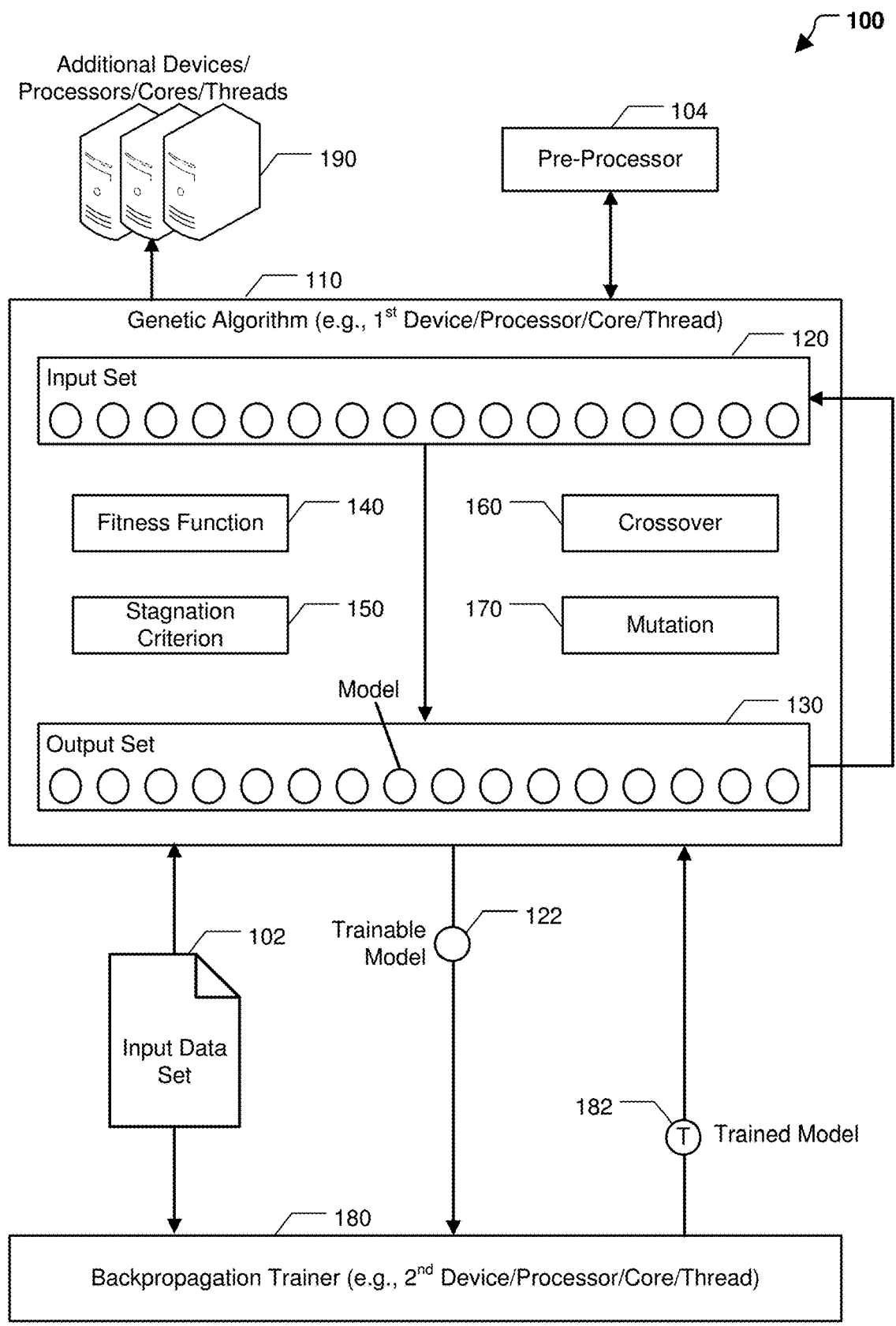
FIG. 1 illustrates a particular example of a system that is operable to support cooperative execution of a genetic algorithm and a backpropagation trainer.

Referring to FIG. 1, a particular illustrative example of a system 100 is shown. The system 100, or portions thereof, may be implemented using (e.g., executed by) one or more computing devices, such as laptop computers, desktop computers, mobile devices, servers, and Internet of Things devices and other devices utilizing embedded processors and firmware or operating systems, etc. In the illustrated example, the system 100 includes a genetic algorithm 110 and a backpropagation trainer 180. The backpropagation trainer 180 is an example of an optimization trainer, and other examples of optimization trainers that may be used in conjunction with the described techniques include, but are not limited to, a derivative free optimizer (DFO), an extreme learning machine (ELM), etc. The combination of the genetic algorithm 110 and an optimization trainer, such as the backpropagation trainer 180, may be referred to herein as an "automated model building (AMB) engine." In some examples, the AMB engine may include or execute the genetic algorithm 110 but not the backpropagation trainer 180, for example as further described below for reinforcement learning problems.

In particular aspects, the genetic algorithm 110 is executed on a different device, processor (e.g., central processor unit (CPU), graphics processing unit (GPU) or other type of processor), processor core, and/or thread (e.g., hardware or software thread) than the backpropagation trainer 180. The genetic algorithm 110 and the backpropagation trainer 180 may cooperate to automatically generate a neural network model of a particular data set, such as an illustrative input data set 102. In particular aspects, the system 100 includes a pre-processor 104 that is communicatively coupled to the genetic algorithm 110. Although FIG. 1 illustrates the pre-processor 104 as being external to the genetic algorithm 110, it is to be understood that in some examples the pre-processor may be executed on the same device, processor, core, and/or thread as the genetic algorithm 110. Moreover, although referred to herein as an "input" data set 102, the input data set 102 may not be the same as "raw" data sources provided to the pre-processor 104. Rather, as further described herein, the pre-processor 104 may perform various rule-based operations on such "raw" data sources to determine the input data set 102 that is operated on by the automated model building engine. For example, such rule-based operations may scale, clean, and modify the "raw" data so that the input data set 102 is compatible with and/or provides computational benefits (e.g., increased model generation speed, reduced model generation memory footprint, etc.) as compared to the "raw" data sources.

As further described herein, the system 100 may provide an automated data-driven model building process that enables even inexperienced users to quickly and easily build highly accurate models based on a specified data set. Additionally, the system 100 simplify the neural network model to avoid overfitting and to reduce computing resources required to run the model.

The genetic algorithm 110 includes or is otherwise associated with a fitness function 140, a stagnation criterion 150, a crossover operation 160, and a mutation operation 170. As described above, the genetic algorithm 110 may represent a recursive search process. Consequently, each iteration of the search process (also called an epoch or generation of the genetic algorithm) may have an input set (or population) 120 and an output set (or population) 130. The input set 120 of an initial epoch of the genetic algorithm 110 may be randomly or pseudo-randomly generated. After that, the output set 130 of one epoch may be the input set 120 of the next (non-initial) epoch, as further described herein.

The input set 120 and the output set 130 may each include a plurality of models, where each model includes data representative of a neural network. For example, each model may specify a neural network by at least a neural network topology, a series of activation functions, and connection weights. The topology of a neural network may include a configuration of nodes of the neural network and connections between such nodes. The models may also be specified to include other parameters, including but not limited to bias values/functions and aggregation functions.

Figure 2:
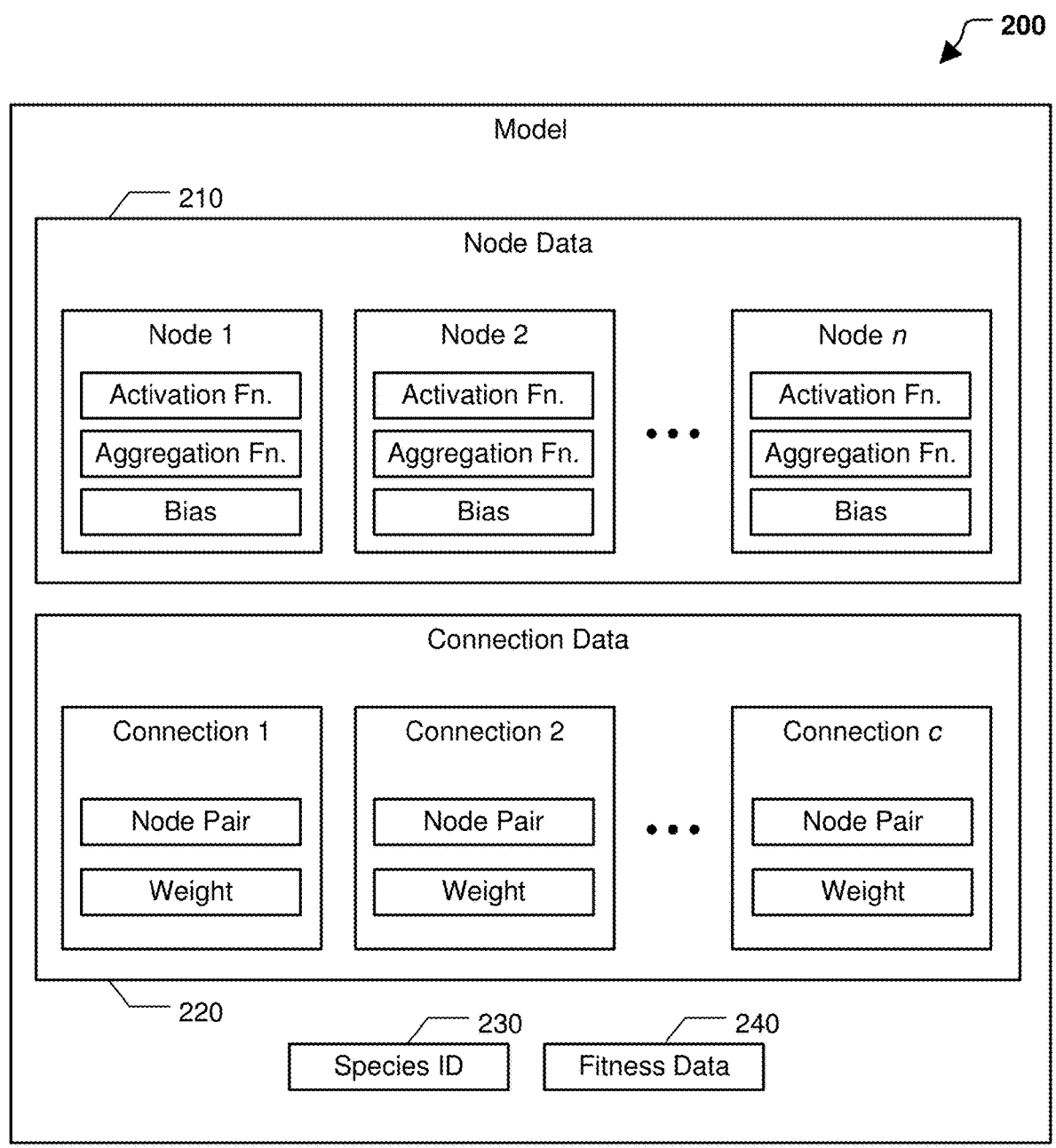
FIG. 2 illustrates a particular example of a model including data representative of a neural network.

Additional examples of neural network models are further described with reference to FIG. 2. In particular, as shown in FIG. 2, a model 200 may be a data structure that includes node data 210 and connection data 220. In the illustrated example, the node data 210 for each node of a neural network may include at least one of an activation function, an aggregation function, or a bias (e.g., a constant bias value or a bias function). The activation function of a node may be a step function, sine function, continuous or piecewise linear function, sigmoid function, hyperbolic tangent function, or other type of mathematical function that represents a threshold at which the node is activated. The biological analog to activation of a node is the firing of a neuron. The aggregation function may be a mathematical function that combines (e.g., sum, product, etc.) input signals to the node. An output of the aggregation function may be used as input to the activation function. The bias may be a constant value or function that is used by the aggregation function and/or the activation function to make the node more or less likely to be activated.

The connection data 220 for each connection in a neural network may include at least one of a node pair or a connection weight. For example, if a neural network includes a connection from node N1 to node N2, then the connection data 220 for that connection may include the node pair <N1, N2>. The connection weight may be a numerical quantity that influences if and/or how the output of N1 is modified before being input at N2. In the example of a recurrent network, a node may have a connection to itself (e.g., the connection data 220 may include the node pair <N1, N1>).

The model 200 may also include a species identifier (ID) 230 and fitness data 240. The species ID 230 may indicate which of a plurality of species the model 200 is classified in, as further described with reference to FIG. 7. The fitness data 240 may indicate how well the model 200 models the input data set 102. For example, the fitness data 240 may include a fitness value that is determined based on evaluating the fitness function 140 with respect to the model 200, as further described herein.

Returning to FIG. 1, the fitness function 140 may be an objective function that can be used to compare the models of the input set 120. In some examples, the fitness function 140 is based on a frequency and/or magnitude of errors produced by testing a model on the input data set 102. As a simple example, assume the input data set 102 includes ten rows, that the input data set 102 includes two columns denoted A and B, and that the models illustrated in FIG. 1 represent neural networks that output a predicted a value of B given an input value of A. In this example, testing a model may include inputting each of the ten values of A from the input data set 102, comparing the predicted values of B to the corresponding actual values of B from the input data set 102, and determining if and/or by how much the two predicted and actual values of B differ. To illustrate, if a particular neural network correctly predicted the value of B for nine of the ten rows, then the a relatively simple fitness function 140 may assign the corresponding model a fitness value of $9/10=0.9$. It is to be understood that the previous example is for illustration only and is not to be considered limiting. In some aspects, the fitness function 140 may be based on factors unrelated to error frequency or error rate, such as number of input nodes, node layers, hidden layers, connections, computational complexity, etc.

In a particular aspect, fitness evaluation of models may be performed in parallel. To illustrate, the system 100 may include additional devices, processors, cores, and/or threads 190 to those that execute the genetic algorithm 110 and the backpropagation trainer 180. These additional devices, processors, cores, and/or threads 190 may test model fitness in parallel based on the input data set 102 and may provide the resulting fitness values to the genetic algorithm 110.

In a particular aspect, the genetic algorithm 110 may be configured to perform speciation. For example, the genetic algorithm 110 may be configured to cluster the models of the input set 120 into species based on "genetic distance" between the models. Because each model represents a neural network, the genetic distance between two models may be based on differences in nodes, activation functions, aggregation functions, connections, connection weights, etc. of the two models. In an illustrative example, the genetic algorithm 110 may be configured to serialize a model into a bit string. In this example, the genetic distance between models may be represented by the number of differing bits in the bit strings corresponding to the models. The bit strings corresponding to models may be referred to as "encodings" of the models. Speciation is further described with reference to FIG. 7.

Because the genetic algorithm 110 is configured to mimic biological evolution and principles of natural selection, it may be possible for a species of models to become "extinct." The stagnation criterion 150 may be used to determine when a species should become extinct, e.g., when the models in the species are to be removed from the genetic algorithm 110. Stagnation is further described with reference to FIG. 8.

The crossover operation 160 and the mutation operation 170 is highly stochastic under certain constraints and a defined set of probabilities optimized for model building, which produces reproduction operations that can be used to generate the output set 130, or at least a portion thereof, from the input set 120. In a particular aspect, the genetic algorithm 110 utilizes intra-species reproduction but not inter-species reproduction in generating the output set 130. Including intra-species reproduction and excluding inter-species reproduction may be based on the assumption that because they share more genetic traits, the models of a species are more likely to cooperate and will therefore more quickly converge on a sufficiently accurate neural network. In some examples, inter-species reproduction may be used in addition to or instead of intra-species reproduction to generate the output set 130. Crossover and mutation are further described with reference to FIG. 10.

Left alone and given time to execute enough epochs, the genetic algorithm 110 may be capable of generating a model (and by extension, a neural network) that meets desired accuracy requirements. However, because genetic algorithms utilize randomized selection, it may be overly time-consuming for a genetic algorithm to arrive at an acceptable neural network. In accordance with the present disclosure, to "help" the genetic algorithm 110 arrive at a solution faster, a model may occasionally be sent from the genetic algorithm 110 to the backpropagation trainer 180 for training. This model is referred to herein as a trainable model 122. In particular, the trainable model 122 may be based on crossing over and/or mutating the fittest models of the input set 120, as further described with reference to FIG. 9. Thus, the trainable model 122 may not merely be a genetically "trained" file produced by the genetic algorithm 110. Rather, the trainable model 122 may represent an advancement with respect to the fittest models of the input set 120.

The backpropagation trainer 180 may utilize a portion, but not all of the input data set 102 to train the connection weights of the trainable model 122, thereby generating a trained model 182. For example, the portion of the input data set 102 may be input into the trainable model 122, which may in turn generate output data. The input data set 102 and the output data may be used to determine an error value, and the error value may be used to modify connection weights of the model, such as by using gradient descent or another function.

The backpropagation trainer 180 may train using a portion rather than all of the input data set 102 to mitigate overfit concerns and/or to shorten training time. The backpropagation trainer 180 may leave aspects of the trainable model 122 other than connection weights (e.g., neural network topology, activation functions, etc.) unchanged. Backpropagating a portion of the input data set 102 through the trainable model 122 may serve to positively reinforce "genetic traits" of the fittest models in the input set 120 that were used to generate the trainable model 122. Because the backpropagation trainer 180 may be executed on a different device, processor, core, and/or thread than the genetic algorithm 110, the genetic algorithm 110 may continue executing additional epoch(s) while the connection weights of the trainable model 122 are being trained. When training is complete, the trained model 182 may be input back into (a subsequent epoch of) the genetic algorithm 110, so that the positively reinforced "genetic traits" of the trained model 182 are available to be inherited by other models in the genetic algorithm 110.

Operation of the system 100 is now described with reference to FIGS. 3-11. It is to be understood, however, that in alternative implementations certain operations may be performed in a different order than described. Moreover, operations described as sequential may be instead be performed at least partially concurrently, and operations described as being performed at least partially concurrently may instead be performed sequentially.

During a configuration stage of operation, a user may specify data sources from which the pre-processor 104 is to determine the input data set 102. The user may also specify a particular data field or a set of data fields in the input data set 102 to be modeled. The pre-processor 104 may determine the input data set 102, determine a machine learning problem type to be solved, and initialize the AMB engine (e.g., the genetic algorithm 110 and/or the backpropagation trainer 180) based on the input data set 102 and the machine learning problem type. As an illustrative non-limiting example, the pre-processor 104 may determine that the data field(s) to be modeled corresponds to output nodes of a neural network that is to be generated by the system 100. For example, if a user indicates that the value of a particular data field is to be modeled (e.g., to predict the value based on other data of the data set), the model may be generated by the system 100 to include an output node that generates an output value corresponding to a modeled value of the particular data field. In particular implementations, the user can also configure other aspects of the model. For example, the user may provide input to indicate a particular data field of the data set that is to be included in the model or a particular data field of the data set that is to be omitted from the model. As another example, the user may provide input to constrain allowed model topologies. To illustrate, the model may be constrained to include no more than a specified number of input nodes, no more than a specified number of hidden layers, or no recurrent loops.

Further, in particular implementations, the user can configure aspects of the genetic algorithm 110, such as via input to the pre-processor 104 or graphical user interfaces (GUIs) generated by the pre-processor 104. For example, the user may provide input to limit a number of epochs that will be executed by the genetic algorithm 110. Alternatively, the user may specify a time limit indicating an amount of time that the genetic algorithm 110 has to generate the model, and the genetic algorithm 110 may determine a number of epochs that will be executed based on the specified time limit. To illustrate, an initial epoch of the genetic algorithm 110 may be timed (e.g., using a hardware or software timer at the computing device executing the genetic algorithm 110), and a total number of epochs that are to be executed within the specified time limit may be determined accordingly. As another example, the user may constrain a number of models evaluated in each epoch, for example by constraining the size of the input set 120 and/or the output set 130. As yet another example, the user can define a number of trainable models 122 to be trained by the backpropagation trainer 180 and fed back into the genetic algorithm 110 as trained models 182.

In particular aspects, configuration of the genetic algorithm 110 by the pre-processor 104 includes performing other pre-processing steps. For example, the pre-processor 104 may determine whether a neural network is to be generated for a regression problem, a classification problem, a reinforcement learning problem, etc. As another example, the input data set 102 may be "cleaned" to remove obvious errors, fill in data "blanks," etc. in the data source(s) from which the input data set 102 is generated. As another example, values in the input data set 102 may be scaled (e.g., to values between 0 and 1) relative to values in the data source(s). As yet another example, non-numerical data (e.g., categorical classification data or Boolean data) in the data source(s) may be converted into numerical data or some other form of data that is compatible for ingestion and processing by a neural network. Thus, the pre-processor 104 may serve as a "front end" that enables the same AMB engine to be driven by input data sources for multiple types of computing problems, including but not limited to classification problems, regression problems, and reinforcement learning problems.

Figure 3:
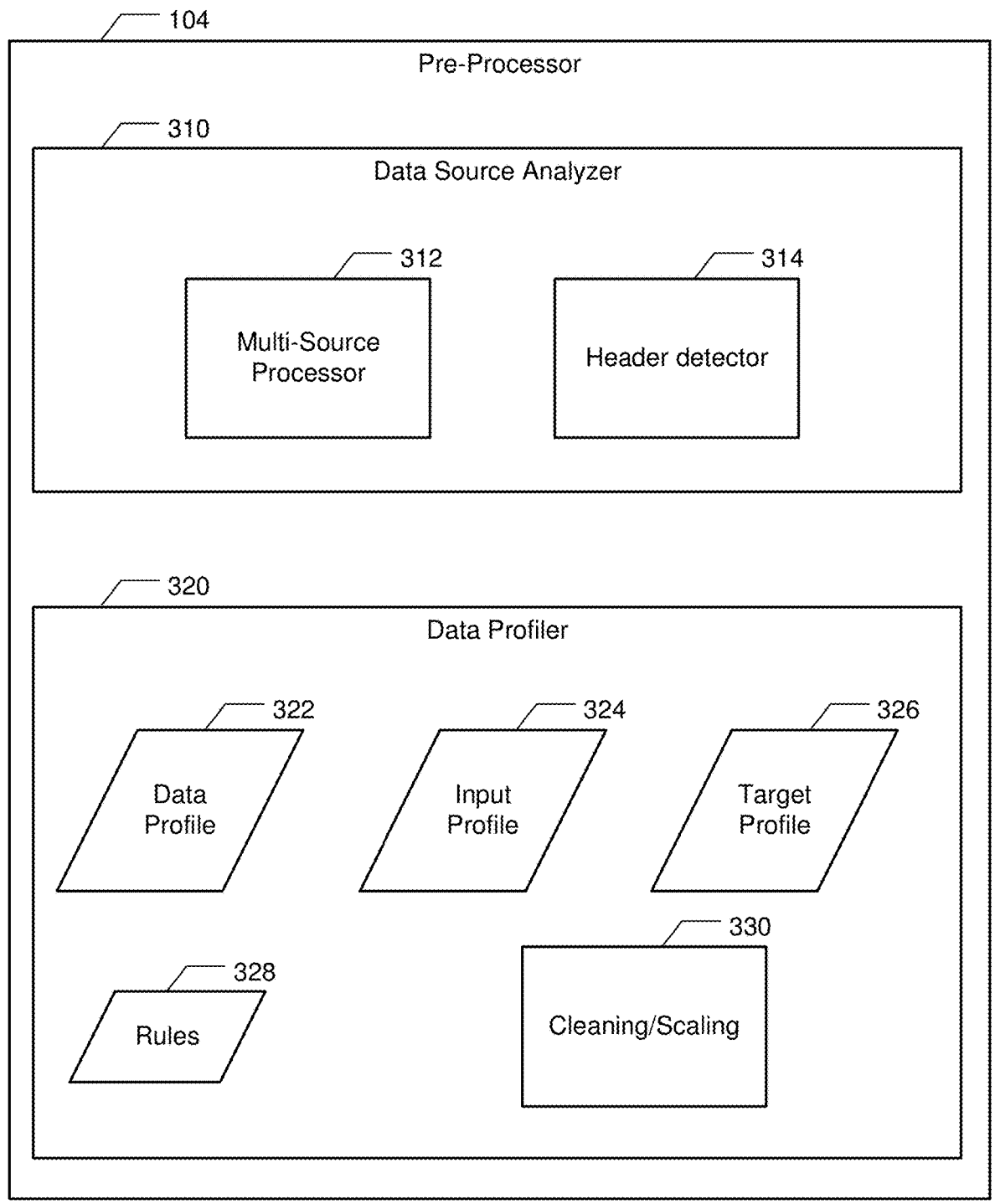
FIG. 3 illustrates a particular example of a pre-processor that is operable to enable data-driven automated model building.

Additional examples of operation at the pre-processor 104 are further described with reference to FIGS. 3-6. For example, referring to FIG. 3, the pre-processor 104 may include a data source analyzer 310. It is to be understood that the pre-processor 104 and/or components thereof may be implemented using dedicated hardware, software (e.g., instructions executed by a processor), or a combination thereof. Moreover, different components of the pre-processor 104 may be implemented using the same or different hardware and/or software. Thus, the specific organization of the pre-processor 104 shown in FIG. 3 is for illustrative purposes only and is not to be considered limiting.

The data source analyzer 310 may analyze data sources that are provided for automated model building. Examples of data sources include, but are not limited to, a file, a directory of multiple files, structured query language (SQL) servers, database servers, data archives, etc. When the data source analyzer 310 processes multiple distinct data sources, such as multiple tables, a multi-source processor 312 may automatically generate a combined data source that can serve as the basis for generating the input data set 102 to be provided to the automated model building engine. In a particular example, the combined data source is a single table that organizes data from each of multiple files, where the pre-processor 104 may add, remove, and/or rename certain columns. To illustrate, consider a system that includes multiple sensors, where each sensor generates timestamped readings that are stored in a file for that sensor. Each row of the file may include a timestamp and a reading, and the name of the file may include a sensor ID of the sensor. In this example, determining the combined data source may include operations such as concatenating the files and adding a sensor ID column that is populated for each row based on the file name of the file the row was originally included in.

In some examples, the data source analyzer 310 includes a header detector 314. To illustrate, if a data source is or includes a table, then columns of the table may represent different data fields. The header detector 314 may determine whether the columns of the table have a header row with column labels. If so, such labels may be used as column names (e.g., in GUIs such as those shown in FIGS. 4-6), but redundant copies of the labels may be removed before portions of the tables are joined.

The pre-processor 104 may also include a data profiler 320 that examines data fields (e.g., columns) and determines various information regarding the data fields based on application of one or more rules 328. To illustrate, the data profile 320 may determine the type of data in each column, such as numerical data, categorical data, date/time data, etc. Categorical data may include alphanumeric strings or numerical "classification" values. To illustrate, a table may include a "quartile" column in which each row has the value 1, 2, 3, or 4. Although the values in the column are numeric, it will be appreciated that the quartile column includes categorical data, because it categorizes each row into one of four quartiles. Thus, in a particular example, the data profiler 320 may determine that a column of numbers includes categorical data rather than numerical data based on determining that the column includes fewer than a threshold number of unique values.

The data profiler 320 may also determine whether any data fields should be "dropped," e.g., removed from the combined data source, left out of the input data set 102, and/or otherwise not provided to the automated model building engine. For example, the data profiler 320 may drop a column that has zero standard deviation (e.g., because a column that has the same value in each row is unlikely to be an input feature of a neural network). As another example, the data profiler 320 may drop a column that is determined to be an identifier column. An identifier column may include a unique value for every row or at least a threshold percentage of the rows, such as 80%, and such columns may also have a low likelihood of being an input feature of a neural network. As another example, the data profiler 320 may drop a column that has at least a threshold percentage of missing or corrupted values. To illustrate, a missing value may be detected by detecting two adjacent commas in a CSV file and non-alphanumeric values may be considered corrupt values. The data profiler 320 may drop columns that have more than a threshold percentage (e.g., 80%) of missing data. The data profiler 320 may also drop categorical columns that include more than a threshold number of unique values (e.g., to avoid memory overflow when each unique value is processed as a separate one-hot encoded column, as further described herein).

The data profiler 320 may generate a data profile 322 that includes information regarding each of the data fields included in the combined data source. For example, the data profile 322 may be represented as a table, where each row of the table represents a data field. Each row may include a name of the data field (e.g., as determined by the header detector 314 or as automatically assigned if the header detector 314 determines that no columns labels are present). Each row may also include a type of the data field (e.g., numerical, categorical, time/date, etc.). Each row may further include statistical metrics regarding the data field, such as minimum, maximum, mean, standard deviation, etc.

In some aspects, the data profile 322 may be used to generate an input profile 324 and a target profile 326. The input profile 324 may include information for data fields that are available for use as potential input nodes of a neural network determined by the automated model building engine. The target profile 326 (alternatively referred to as an output profile) may include information for data fields that are to be modeled by the neural network. Thus, the target profile 326 may correspond to the output node(s) of the neural network.

The data profiler 320 may also perform cleaning/scaling operations 330 on data. An illustrative non-limiting example of a data cleaning operation is to perform imputation to determine missing data values. Examples of imputation include, but are not limited to, forward filling, back filling, and filling using a mean of valid values from surrounding rows.

An illustrative non-limiting example of a data scaling operation is "compressing" the range of a numerical column. To illustrate, a column of values from 0 to several thousand may be converted to a column of values between zero and one. Another illustrative non-limiting example is to convert a column of categorical values to multiple columns according to a one-hot encoding scheme. For example, a "quartile" column in which each row can have the value 1, 2, 3, or 4 may be replaced by four columns called "quartile 1," "quartile 2," "quartile 3," and "quartile 4," where each row has a value of 1 in one of the four columns and has a value of zero in the other three columns. In some aspects, the data profiler 320 may maintain a record of the scaling operations that have been performed, so that inverse scaling operations may be performed, for example on regression-based prediction output of a neural network.

Although not shown in FIG. 3, in particular aspects the data profiler 320 or the data source analyzer 310 may perform data splitting operations. For example, the combined data source may be divided into training and testing sets, which may potentially include multiple testing sets for crossfold validation. Thus, it is to be understood that although the input data set 102 is shown in FIG. 1 as a single data set, the input data set 102 may represent one or more training sets and one or more testing sets.

In some examples, the pre-processor 104 is configured to generate graphical user interfaces (GUIs) that may be sent to a display device, such as a display device of or coupled to a computing device associated with pre-processor 104. The GUIs may receive input for use by the data source analyzer 310, the data profiler 320, and/or the automated model building engine (e.g., the genetic algorithm 110 and/or the backpropagation trainer 180). For example, FIG. 4 illustrates examples of GUIs that enable a user to indicate data source(s) and indicate that a neural network is to be generated that predicts the value of one of the numerical data fields of the data set (e.g., a regression machine learning problem).

In the illustrated examples, the user initiates automated model building to predict malignancy diagnoses for breast cancer based on training using the Wisconsin Diagnostic Breast Cancer (WDBC) data set. The WDBC data set is a freely available benchmark machine learning data set from the University of Wisconsin hospitals. In a first GUI 410, the user names the model to be built "WDBC Predict," specifies a maximum training time of 15 minutes, and indicates that this is a supervised machine learning problem. In a second GUI 420, the user initiates an upload of the WDBC data set, which in this example is a comma-separated values (CSV) file called WDBC.csv.

After the WDBC data set is uploaded, the user indicates that the goal is to predict a target column, as shown in a third GUI 430. In the WDBC data set, each row corresponds to a patient and includes thirty-two columns. The columns include a patient ID column and a diagnosis column that can have a value of M (malignant) or B (benign). The columns also include thirty numerical feature columns, namely mean, standard error, and "worst" (i.e., largest) values for each of ten tumor characteristics: radius, texture, perimeter, area, smoothness, compactness, concavity, concave points, symmetry, and fractal dimension. As shown in FIG. 4, the user identifies the diagnosis column as the prediction target.

Based on the above input received via the GUIs 410-440, the pre-processor 104 may perform various operations. For example, the pre-processor 104 may determine that because the prediction target is a categorical column, a neural network is to be generated for a classification problem rather than a regression problem or a reinforcement learning problem.

As another example, the pre-processor 104 may set the target profile 326 so that the automated model engine generates the neural network to have two output nodes, where one output node indicates the probability of a malignant diagnosis and the other output node indicates the probability of a benign diagnosis. The final classification output of the neural network may be based on a softmax of the probabilities. As another example, the pre-processor 104 may drop the patient ID column. The pre-processor 104 may scale/clean one or more of the thirty numerical feature columns and split the data into training/testing sets. The pre-processor 104 may provide the resulting data as the input data set 102 for the automated model building engine.

FIG. 5 illustrates examples of GUIs that may be used to predict a numerical value. In particular, as shown by a GUI 540, the mean tumor radius is to be predicted rather than a malignant/benign diagnosis. Thus, in this example, the pre-processor 104 determines that a neural network is to be generated for a regression problem. The pre-processor 104 may also convert the categorical diagnosis column into two separate columns (e.g., "Diagnosis-B" and "Diagnosis-M") in accordance with a one-hot encoding scheme.

Although the examples of FIGS. 4 and 5 illustrate data-driven automated model building to predict classification and regression output, respectively, it should be understood that the techniques of the present disclosure may also provide data-driven model building for additional/different problem types in healthcare and non-healthcare environments.

For example, a folder may include multiple files, where each file includes timestamped data from individual wind turbines on a wind farm. As shown in a GUI 620 of FIG. 6A, the user may indicate such a folder as including the data set(s) to be uploaded. It may be useful to generate a neural network that can predict, based on wind turbine sensor readings, if and when a wind turbine is likely to fail in the future. Thus, the user may select "Forecast Failures" rather than "Predict Target(s)" in a GUI 630. The user may then indicate that a "Turbine ID" column identifies the assets (e.g., wind turbines) whose failures are to be predicted, and that the predictions should provide a minimum lead time (e.g., 3 days in the illustrated example), as shown in a GUI 640.

Next, the user may upload or manually enter known failures, such as past time periods during which individual wind turbines were known to be in a failure state. A first GUI 650 of FIG. 6B illustrates manual failure entry by selecting a wind turbine from a drop-down menu and entering the start and end of the failure time period. GUIs 660-670, on the other hand, illustrate uploading a "Failures.csv" file and identifying asset name, failure start, and failure end columns in the file, so that failure information can be automatically extracted by the pre-processor 104.

Regardless of whether failures are entered manually or uploaded automatically, the pre-processor 104 may perform various operations based on the received input shown in FIGS. 6A and 6B. For example, the pre-processor 104 may determine that a neural network is to be generated to solve a combined classification/regression problem that predicts, based on windfarm sensor data, a likelihood of failure at least a particular number of days in advance (e.g., the minimum lead time of the GUI 640). For a combined classification/regression problem that includes a mix of numerical and categorical targets, the neural network may include an output node for each numerical target and may include an output node for each category. Categorical outputs may be input into a softmax function, as explained above. As another example, the pre-processor 104 may scale/clean data and generate input and output data profiles, as described with reference to FIG. 3.

In particular aspects, the pre-processor 104 may select an error function that is to be used by the AMB engine when evaluating neural networks. For example, if the pre-processor 104 determines that a neural network is to be generated for a classification problem, the error function may be a cross entropy error function that is based on a number of correct vs. incorrect classifications. As another example, if the pre-processor 104 determines that a neural network is to be determined for a regression problem, the error function may be a mean square error function.

In particular aspects, the pre-processor 104 may perform imbalance compensation. For example, consider a classification problem to predict one of two states: success and failure. If a large percentage (e.g., 90%) of available data is for the success state and a small percentage (e.g., 10%) of the available data is for the failure state, models generated via neuroevolution may erroneously predict success around 90% of the time rather than evolving to appropriately consider other input factors. To compensate for the imbalance in the available data, the pre-processor 104 may determine data sampling criteria. To illustrate, the input data set 102 for the AMB engine may be generated from available data sources to provide approximately a 50%-50% split between the success and failure states.

GUIs may also be used to initiate automated model building for reinforcement learning. As an illustrative non-limiting example, such GUIs may enable a user to indicate or upload a state data structure and/or an action data structure. The GUIs may also enable the user to indicate a number of simulation repetitions. The GUIs may further enable the user to indicate or upload a reward function that is calculated based on the state data structure and an interaction function that applies the action data structure to the simulation. For example, a neural network to output aircraft auto-pilot operations may be generated and trained using reinforcement learning techniques. In such an example, the actions data structure may include throttle, steer, flaps, etc., and the reward function may be based on aircraft altitude, aircraft distance traveled, etc. In particular aspects, if the pre-processor 104 determines that a neural network is to be generated for a reinforcement learning problem, the genetic algorithm 110 may be used alone (rather than in conjunction with a trainer, such as the backpropagation trainer 180) to generate the neural network.

Although the pre-processor 104 is described above as performing scaling and/or cleaning operations, in alternative examples such operations may be part of the models evolved by the AMB engine. For example, each model may include data indicating a scaling function and/or a cleaning (e.g., imputation) function. Examples of imputation include, but are not limited to, forward filling, back filling, and mean filling. In this scenario, the scaling/cleaning function(s) indicated by each model may be applied to the input data set 102 prior to determining model fitness, and the scaling/cleaning function(s) may evolve via crossover and mutation operations.

It will thus be appreciated that, as described with reference to FIGS. 3-6, the pre-processor 104 may enable "data-driven" model creation, i.e., "data-driven" automated model building. The described model creation may be considered "data-driven" because the system 100 is not be limited to operating on specific data and does not require a priori knowledge of the type of machine learning problem to be solved by a neural network. Rather, the pre-processor 104 is configured to provide on-demand data scaling, data cleaning, data transformation, and machine learning problem type identification. Consequently, the automated model building engine (e.g., the genetic algorithm 110 and the backpropagation trainer 180) is compatible with various types of data sources and may generate a neural network for multiple types of machine learning problems in a data-agnostic fashion.

Returning to FIG. 1, after the above-described configuration operations by the pre-processor 104 are performed, the automated model building engine may begin execution based on the input data set 102 determined by the pre-processor 104. In some examples, the pre-processor 104 provides one or more parameters to the automated model building engine. Examples of automated model building parameters include, but are not limited to, a maximum number of generations for the genetic algorithm 110, a threshold fitness value that results in termination of the automated model building even if the maximum number of generations has not been reached, the data profile 322, the input profile 324, the target profile 326, whether parallelization of training is enabled, whether to evolve a feedforward or recurrent neural network, etc.

During automated model building, the genetic algorithm 110 may automatically generate an initial set of models based on the input data set 102, received user input indicating (or usable to determine) the type of problem to be solved, etc. (e.g., the initial set of models is data-driven). As illustrated in FIG. 2, each model may be specified by at least a neural network topology, an activation function, and link weights. The neural network topology may indicate an arrangement of nodes (e.g., neurons). For example, the neural network topology may indicate a number of input nodes, a number of hidden layers, a number of nodes per hidden layer, and a number of output nodes. The neural network topology may also indicate the interconnections (e.g., axons or links) between nodes.

The initial set of models may be input into an initial epoch of the genetic algorithm 110 as the input set 120, and at the end of the initial epoch, the output set 130 generated during the initial epoch may become the input set 120 of the next epoch of the genetic algorithm 110. In some examples, the input set 120 may have a specific number of models. For example, as shown in a first stage 700 of operation in FIG. 7, the input set may include 200 models. It is to be understood that alternative examples may include a different number of models in the input set 120 and/or the output set 130.

For the initial epoch of the genetic algorithm 110, the topologies of the models in the input set 120 may be randomly or pseudo-randomly generated within constraints specified by any previously input configuration settings. Accordingly, the input set 120 may include models with multiple distinct topologies. For example, a first model may have a first topology, including a first number of input nodes associated with a first set of data parameters, a first number of hidden layers including a first number and arrangement of hidden nodes, one or more output nodes, and a first set of interconnections between the nodes. In this example, a second model of epoch may have a second topology, including a second number of input nodes associated with a second set of data parameters, a second number of hidden layers including a second number and arrangement of hidden nodes, one or more output nodes, and a second set of interconnections between the nodes. Since the first model and the second model are both attempting to model the same data field(s), the first and second models have the same output nodes.

The genetic algorithm 110 may automatically assign an activation function, an aggregation function, a bias, connection weights, etc. to each model of the input set 120 for the initial epoch. In some aspects, the connection weights are assigned randomly or pseudo-randomly. In some implementations, a single activation function is used for each node of a particular model. For example, a sigmoid function may be used as the activation function of each node of the particular model. The single activation function may be selected based on configuration data. For example, the configuration data may indicate that a hyperbolic tangent activation function is to be used or that a sigmoid activation function is to be used.

Alternatively, the activation function may be randomly or pseudo-randomly selected from a set of allowed activation functions, and different nodes of a model may have different types of activation functions. In other implementations, the activation function assigned to each node may be randomly or pseudo-randomly selected (from the set of allowed activation functions) for each node the particular model. Aggregation functions may similarly be randomly or pseudo-randomly assigned for the models in the input set 120 of the initial epoch. Thus, the models of the input set 120 of the initial epoch may have different topologies (which may include different input nodes corresponding to different input data fields if the data set includes many data fields) and different connection weights. Further, the models of the input set 120 of the initial epoch may include nodes having different activation functions, aggregation functions, and/or bias values/functions.

Continuing to a second stage 750 of operation, each model of the input set 120 may be tested based on the input data set 102 to determine model fitness. For example, the input data set 102 may be provided as input data to each model, which processes the input data set (according to the network topology, connection weights, activation function, etc., of the respective model) to generate output data. The output data of each model may be evaluated using the fitness function 140 to determine how well the model modeled the input data set 102. For example, in the case of a regression problem, the output data may be evaluated by comparing a prediction value in the output data to an actual value in the input data set 102. As another example, in the case of a classification problem, a classifier result indicated by the output data may be compared to a classification associated with the input data set 102 to determine if the classifier result matches the classification in the input data set 102. As yet another example, in the case of a reinforcement learning problem, a reward may be determined (e.g., calculated) based on evaluation of an environment, which may include one or more variables, functions, etc. In a reinforcement learning problem, the fitness function 140 may be the same as or may be based on the reward function(s). Fitness of a model may be evaluated based on performance (e.g., accuracy) of the model, complexity (or sparsity) of the model, or a combination thereof. As a simple example, in the case of a regression problem or reinforcement learning problem, a fitness value may be assigned to a particular model based on an error value associated with the output data of that model or based on the value of the reward function, respectively. As another example, in the case of a classification problem, the fitness value may be assigned based on whether a classification determined by a particular model is a correct classification, or how many correct or incorrect classifications were determined by the model.

In a more complex example, the fitness value may be assigned to a particular model based on both prediction/classification accuracy or reward optimization as well as complexity (or sparsity) of the model. As an illustrative example, a first model may model the data set well (e.g., may generate output data or an output classification with a relatively small error, or may generate a large positive reward function value) using five input nodes (corresponding to five input data fields), whereas a second potential model may also model the data set well using two input nodes (corresponding to two input data fields). In this illustrative example, the second model may be sparser (depending on the configuration of hidden nodes of each network model) and therefore may be assigned a higher fitness value that the first model.

As shown in FIG. 7, the second stage 750 may include clustering the models into species based on genetic distance. In a particular aspect, the species ID 230 of each of the models may be set to a value corresponding to the species that the model has been clustered into.

Continuing to FIG. 8, during a third stage 800 and a fourth stage 850 of operation, a species fitness may be determined for each of the species. The species fitness of a species may be a function of the fitness of one or more of the individual models in the species. As a simple illustrative example, the species fitness of a species may be the average of the fitness of the individual models in the species. As another example, the species fitness of a species may be equal to the fitness of the fittest or least fit individual model in the species. In alternative examples, other mathematical functions may be used to determine species fitness. The genetic algorithm 110 may maintain a data structure that tracks the fitness of each species across multiple epochs. Based on the species fitness, the genetic algorithm 110 may identify the "fittest" species, shaded and denoted in FIG. 8 as "elite species." Although three elite species 810, 820, and 830 are shown in FIG. 8, it is to be understood that in alternate examples a different number of elite species may be identified.

In a particular aspect, the genetic algorithm 110 uses species fitness to determine if a species has become stagnant and is therefore to become extinct. As an illustrative non-limiting example, the stagnation criterion 150 may indicate that a species has become stagnant if the fitness of that species remains within a particular range (e.g., +/−5%) for a particular number (e.g., 5) epochs. If a species satisfies a stagnation criteria, the species and all underlying models may be removed from the genetic algorithm 110. In the illustrated example, species 760 of FIG. 7 is removed, as shown in the third stage 800 through the use of broken lines.

Proceeding to the fourth stage 850, the fittest models of each "elite species" may be identified. The fittest models overall may also be identified. In the illustrated example, the three fittest models of each "elite species" are denoted "elite members" and shown using a hatch pattern. Thus, model 870 is an "elite member" of the "elite species" 820. The three fittest models overall are denoted "overall elites" and are shown using black circles. Thus, models 860, 862, and 864 are the "overall elites" in the illustrated example. As shown in FIG. 8 with respect to the model 860, an "overall elite" need not be an "elite member," e.g., may come from a non-elite species. In an alternate implementation, a different number of "elite members" per species and/or a different number of "overall elites" may be identified.

Figure 9:
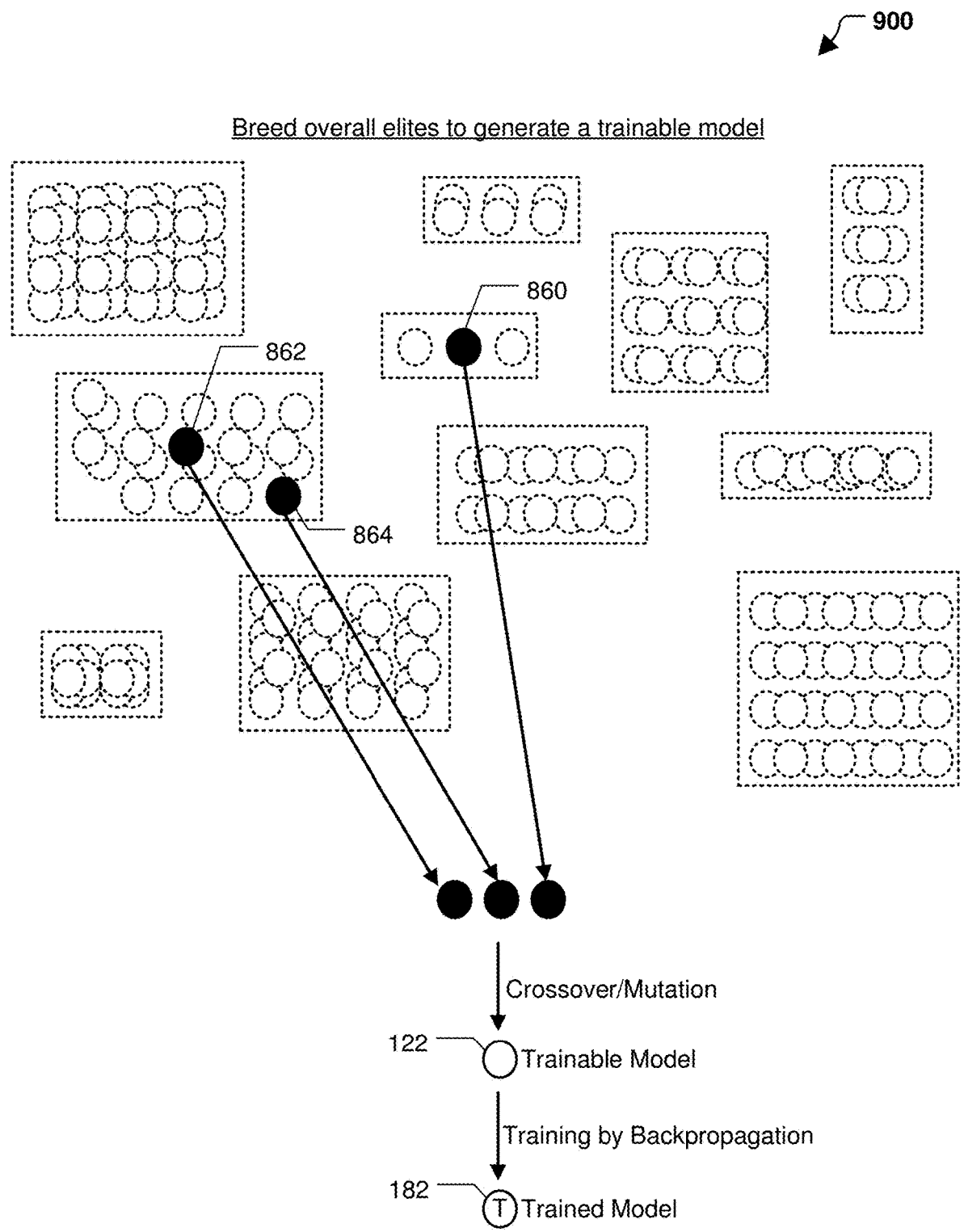
FIG. 9 illustrates a particular example of a fifth stage of operation at the system of FIG. 1.

Referring now to FIG. 9, during a fifth stage 900 of operation, the "overall elite" models 860, 862, and 864 may be genetically combined to generate the trainable model 122. For example, genetically combining models may include crossover operations in which a portion of one model is added to a portion of another model, as further illustrated in FIG. 10. As another example, a random mutation may be performed on a portion of one or more of the "overall elite" models 860, 862, 864 and/or the trainable model 122. The trainable model 122 may be sent to the backpropagation trainer 180, as described with reference to FIG. 1. The backpropagation trainer 180 may train connection weights of the trainable model 122 based on a portion of the input data set 102. When training is complete, the resulting trained model 182 may be received from the backpropagation trainer 180 and may be input into a subsequent epoch of the genetic algorithm 110.

Figure 10:
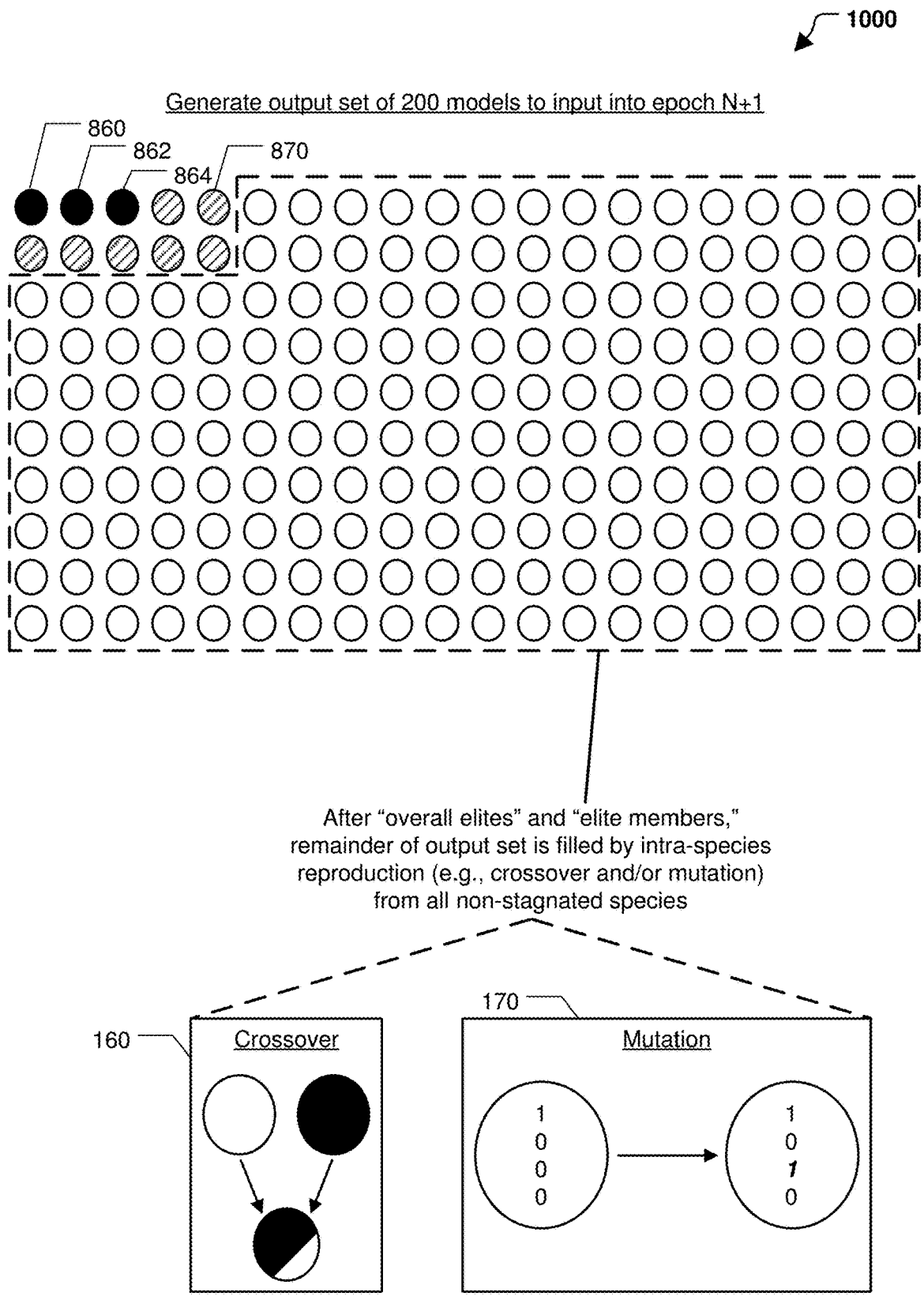
FIG. 10 illustrates a particular example of a sixth stage of operation at the system of FIG. 1.

Continuing to FIG. 10, while the backpropagation trainer 180 trains the trainable model, the output set 130 of the epoch may be generated in a sixth stage 1000 of operation. In the illustrated example, the output set 130 includes the same number of models, e.g., 200 models, as the input set 120. The output set 130 may include each of the "overall elite" models 860-864. The output set 130 may also include each of the "elite member" models, including the model 870. Propagating the "overall elite" and "elite member" models to the next epoch may preserve the "genetic traits" resulted in caused such models being assigned high fitness values.

The rest of the output set 130 may be filled out by random intra-species reproduction using the crossover operation 160 and/or the mutation operation 170. In the illustrated example, the output set 130 includes 10 "overall elite" and "elite member" models, so the remaining 190 models may be randomly generated based on intra-species reproduction using the crossover operation 160 and/or the mutation operation 170. After the output set 130 is generated, the output set 130 may be provided as the input set 120 for the next epoch of the genetic algorithm 110.

During the crossover operation 160, a portion of one model may be combined with a portion of another model, where the size of the respective portions may or may not be equal. To illustrate with reference to the model "encodings" described with respect to FIG. 1, the crossover operation 160 may include concatenating bits 0 to p of one bit string with bits p+1 to q of another bit string, where p and q are integers and p+q is equal to the total size of a bit string that represents a model resulting from the crossover operation 160. When decoded, the resulting bit string after the crossover operation 160 produces a neural network that differs from each of its "parent" neural networks in terms of topology, activation function, aggregation function, bias value/function, link weight, or any combination thereof.

Thus, the crossover operation 160 may be a random or pseudo-random biological operator that generates a model of the output set 130 by combining aspects of a first model of the input set 120 with aspects of one or more other models of the input set 120. For example, the crossover operation 160 may retain a topology of hidden nodes of a first model of the input set 120 but connect input nodes of a second model of the input set to the hidden nodes. As another example, the crossover operation 160 may retain the topology of the first model of the input set 120 but use one or more activation functions of the second model of the input set 120. In some aspects, rather than operating on models of the input set 120, the crossover operation 160 may be performed on a model (or models) generated by mutation of one or more models of the input set 120. For example, the mutation operation 170 may be performed on a first model of the input set 120 to generate an intermediate model and the crossover operation 160 may be performed to combine aspects of the intermediate model with aspects of a second model of the input set 120 to generate a model of the output set 130.

During the mutation operation 170, a portion of a model may be randomly modified. The frequency of mutations may be based on a mutation probability metric, which may be user-defined or randomly selected/adjusted. To illustrate with reference to the model "encodings" described with respect to FIG. 1, the mutation operation 170 may include randomly "flipping" one or more bits a bit string.

The mutation operation 170 may thus be a random or pseudo-random biological operator that generates or contributes to a model of the output set 130 by mutating any aspect of a model of the input set 120. For example, the mutation operation 170 may cause the topology a particular model of the input set to be modified by addition or omission of one or more input nodes, by addition or omission of one or more connections, by addition or omission of one or more hidden nodes, or a combination thereof. As another example, the mutation operation 170 may cause one or more activation functions, aggregation functions, bias values/functions, and/or or connection weights to be modified. In some aspects, rather than operating on a model of the input set, the mutation operation 170 may be performed on a model generated by the crossover operation 160. For example, the crossover operation 160 may combine aspects of two models of the input set 120 to generate an intermediate model and the mutation operation 170 may be performed on the intermediate model to generate a model of the output set 130.

The genetic algorithm 110 may continue in the manner described above through multiple epochs. When the genetic algorithm 110 receives the trained model 182, the trained model 182 may be provided as part of the input set 120 of the next epoch, as shown in a seventh stage 1100 of FIG. 11. For example, the trained model 182 may replace one of the other 200 models in the input set 120 or may be a 201' model of the input set (e.g., in some epochs, more than 200 models may be processed). During training by the backpropagation trainer 180, the genetic algorithm 110 may have advanced one or more epochs. Thus, when the trained model 182 is received, the trained model 182 may be inserted as input into an epoch subsequent to the epoch during which the corresponding trainable model 122 was provided to the backpropagation trainer 180. To illustrate, if the trainable model 122 was provided to the backpropagation trainer 180 during epoch N, then the trained model 182 may be input into epoch N+X, where X is an integer greater than zero.

Figure 11:
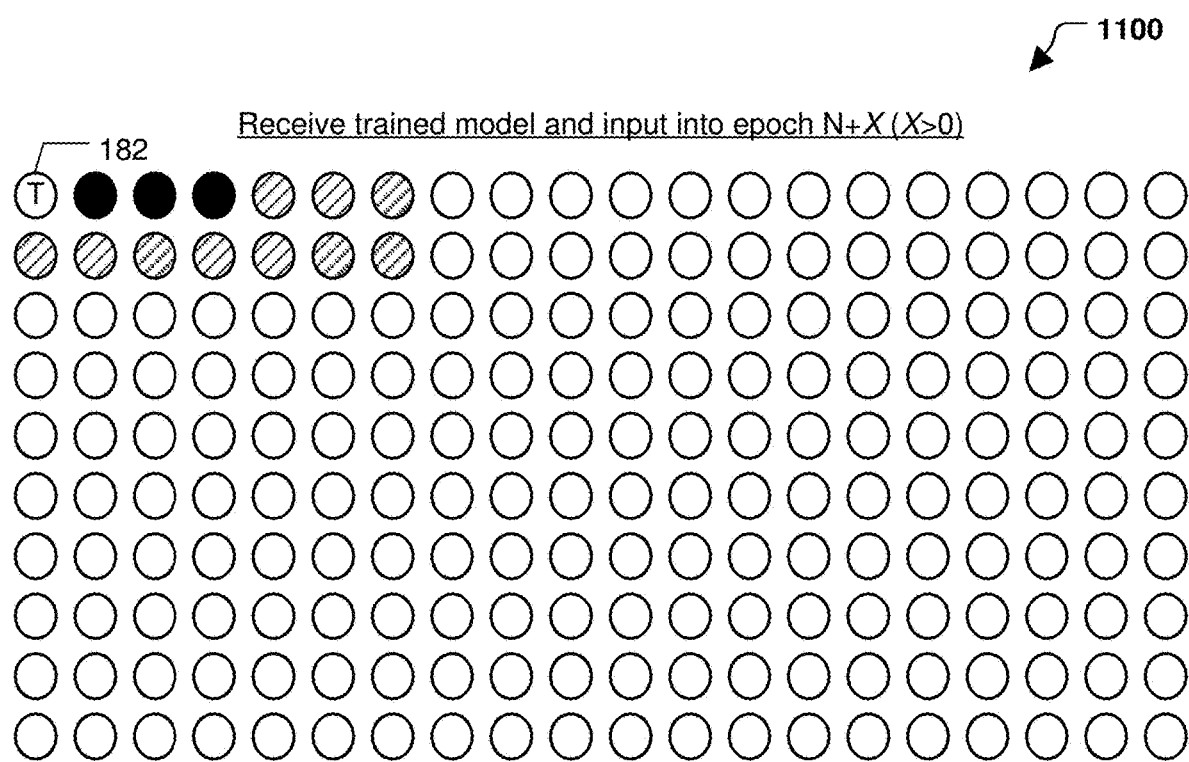
FIG. 11 illustrates a particular example of a seventh stage of operation at the system of FIG. 1.

In the example of FIGS. 9 and 11, a single trainable model 122 is provided to the backpropagation trainer 180 and a single trained model 182 is received from the backpropagation trainer 180. When the trained model 182 is received, the backpropagation trainer 180 becomes available to train another trainable model. Thus, because training takes more than one epoch, trained models 182 may be input into the genetic algorithm 110 sporadically rather than every epoch after the initial epoch. In some implementations, the backpropagation trainer 180 may have a queue or stack of trainable models 122 that are awaiting training. The genetic algorithm 110 may add trainable models 122 to the queue or stack as they are generated and the backpropagation trainer 180 may remove a training model 122 from the queue or stack at the start of a training cycle. In some implementations, the system 100 includes multiple backpropagation trainers 180 (e.g., executing on different devices, processors, cores, or threads). Each of the backpropagation trainers 180 may be configured to simultaneously train a different trainable model 122 to generate a different trained model 182. In such examples, more than one trainable model 122 may be generated during an epoch and/or more than one trained model 182 may be input into an epoch.

Operation at the system 100 may continue iteratively until specified a termination criterion, such as a time limit, a number of epochs, or a threshold fitness value (of an overall fittest model) is satisfied. When the termination criterion is satisfied, an overall fittest model of the last executed epoch may be selected and output as representing a neural network that best models the input data set 102. In some examples, the overall fittest model may undergo a final training operation (e.g., by the backpropagation trainer 180) before being output.

Although various aspects are described with reference to a backpropagation training, it is to be understood that in alternate implementations different types of training may also be used in the system 100. For example, models may be trained using a genetic algorithm training process. In this example, genetic operations similar to those described above are performed while all aspects of a model, except for the connection weight, are held constant.

Performing genetic operations may be less resource intensive than evaluating fitness of models and training of models using backpropagation. For example, both evaluating the fitness of a model and training a model include providing the input data set 102, or at least a portion thereof, to the model, calculating results of nodes and connections of a neural network to generate output data, and comparing the output data to the input data set 102 to determine the presence and/or magnitude of an error. In contrast, genetic operations do not operate on the input data set 102, but rather merely modify characteristics of one or more models. However, as described above, one iteration of the genetic algorithm 110 may include both genetic operations and evaluating the fitness of every model and species. Training trainable models generated by breeding the fittest models of an epoch may improve fitness of the trained models without requiring training of every model of an epoch. Further, the fitness of models of subsequent epochs may benefit from the improved fitness of the trained models due to genetic operations based on the trained models. Accordingly, training the fittest models enables generating a model with a particular error rate in fewer epochs than using genetic operations alone. As a result, fewer processing resources may be utilized in building highly accurate models based on a specified input data set 102.

The system 100 of FIG. 1 may thus support cooperative, data-driven execution of a genetic algorithm and a backpropagation trainer to automatically arrive at an output neural network model of an input data set. The system of FIG. 1 may arrive at the output neural network model faster than using a genetic algorithm or backpropagation alone and with reduced cost as compared to hiring a data scientist. In some cases, the neural network model output by the system 100 may also be more accurate than a model that would be generated by a genetic algorithm or backpropagation alone. The system 100 may also provide a problem-agnostic ability to generate neural networks. For example, the system 100 may represent a single automated model building framework that is capable of generating neural networks for at least regression problems, classification problems, and reinforcement learning problems. Further, the system 100 may enable generation of a generalized neural network that demonstrates improved adaptability to never-before-seen conditions. To illustrate, the neural network may mitigate or avoid overfitting to an input data set and instead may be more universal in nature. Thus, the neural networks generated by the system 100 may be capable of being deployed with fewer concerns about generating incorrect predictions.

It will be appreciated that the systems and methods of the present disclosure may be applicable in various scenarios, infrastructures, and data environments. As an illustrative non-limiting example, the input data set 102 may include timestamped data from a large array of sensors distributed around a wind farm and may also include timestamped uptime/downtime data of individual wind turbines. The system 100 may generate a neural network model that is configured how likely a wind turbine is to fail. The neural network model may, in a particular example, increase failure lead time from 3-5 days to 30-40 days, which can result in reduced downtime and monetary savings for an operator of the wind farm. The system 100 may be capable of automatically building similar kinds of models that predict numerical values or states (e.g., failures) for internet of things (IoT), utilities, and oil/gas infrastructures.

As another illustrative non-limiting example, the input data set 102 may include health data and the system 100 may automatically build a model to predict whether a patient exhibiting certain health conditions is likely to have a particular ailment. As another illustrative non-limiting example, the input data set 102 may include financial data and the system 100 may automatically build a model to forecast market conditions. As another illustrative non-limiting example, the input data set 102 may include network security, network log, and/or malware data, and the system 100 may automatically build a model to implement firewall filtering rules, endpoint anti-malware detection, a bot/botnet detector, etc.

As another illustrative non-limiting example, the system 100 may generate a neural network to output aircraft autopilot operations (e.g. throttle, steer, flaps, etc.) based on reinforcement learning. In such an example, the reward function optimized by the neural network may involve aircraft altitude, aircraft distance traveled, etc. As yet another example, the system 100 may generate a neural network to predict oil/gas industry workover events (e.g., events that lead to major maintenance or remedial operations on a rig or well, which can lead to considerable production time lost and expense incurred).

Yet another example of a problem set that can be solved with neural networks generated with the system described herein is data fusion. In this case, data aggregated from a large number of sensors of various types, including multiple sensors of the same type, is collected and used to identify an object, action or phenomenon that wouldn't be entirely detectable with any one, or a small subset of sensors. For example, the detection of a submarine may be performed based on the inputs received from multiple sonar buoys which provide input to the generated neural network. Another example may be the identification of a particular type of aircraft based on both the audio signature and a visual view (which may be partially obscured, or low resolution).

Figure 12A:
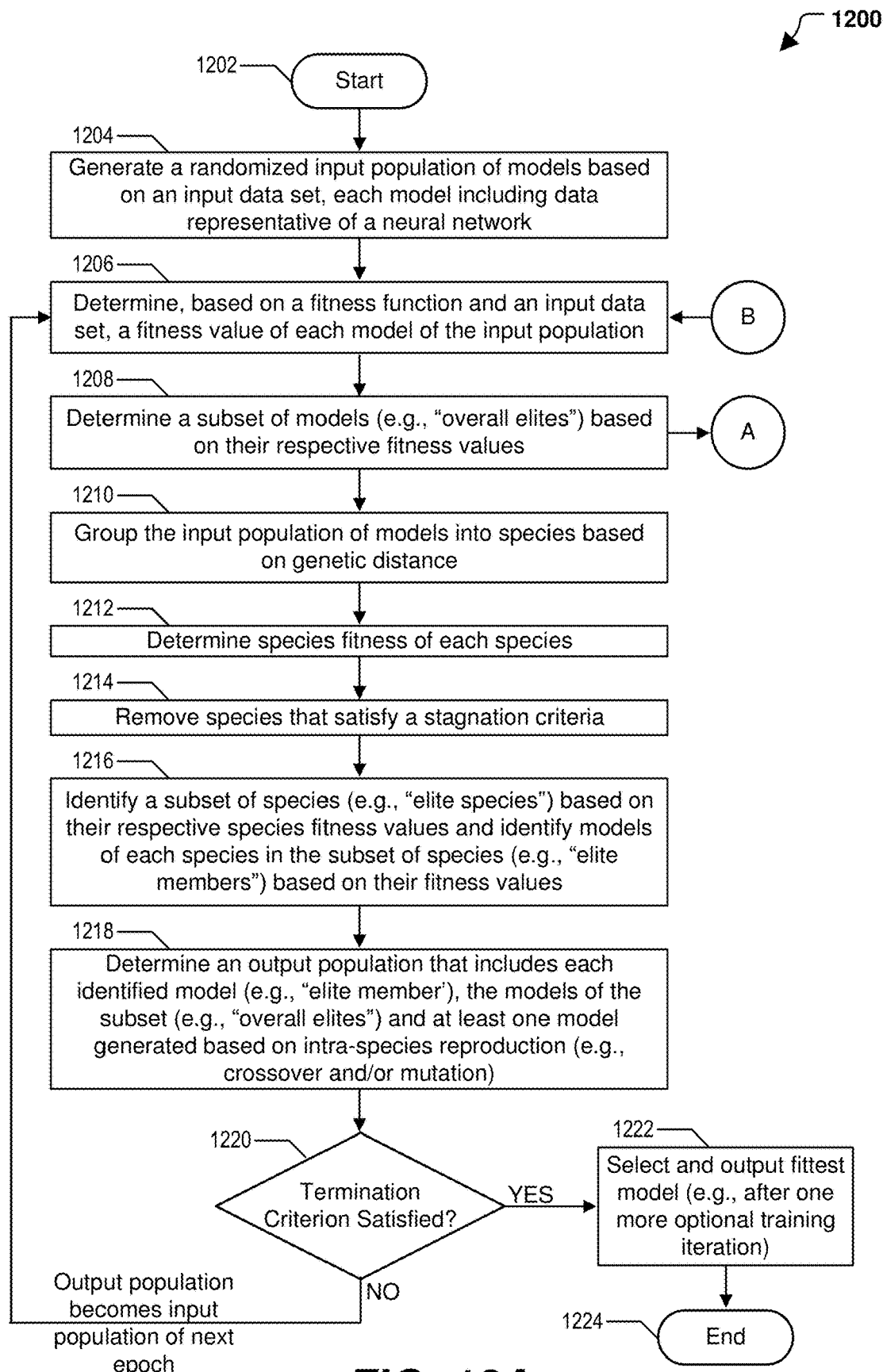
FIGS. 12A and 12B collectively illustrate a particular example of a method of cooperative execution of a genetic algorithm and a backpropagation trainer.
Figure 12B:
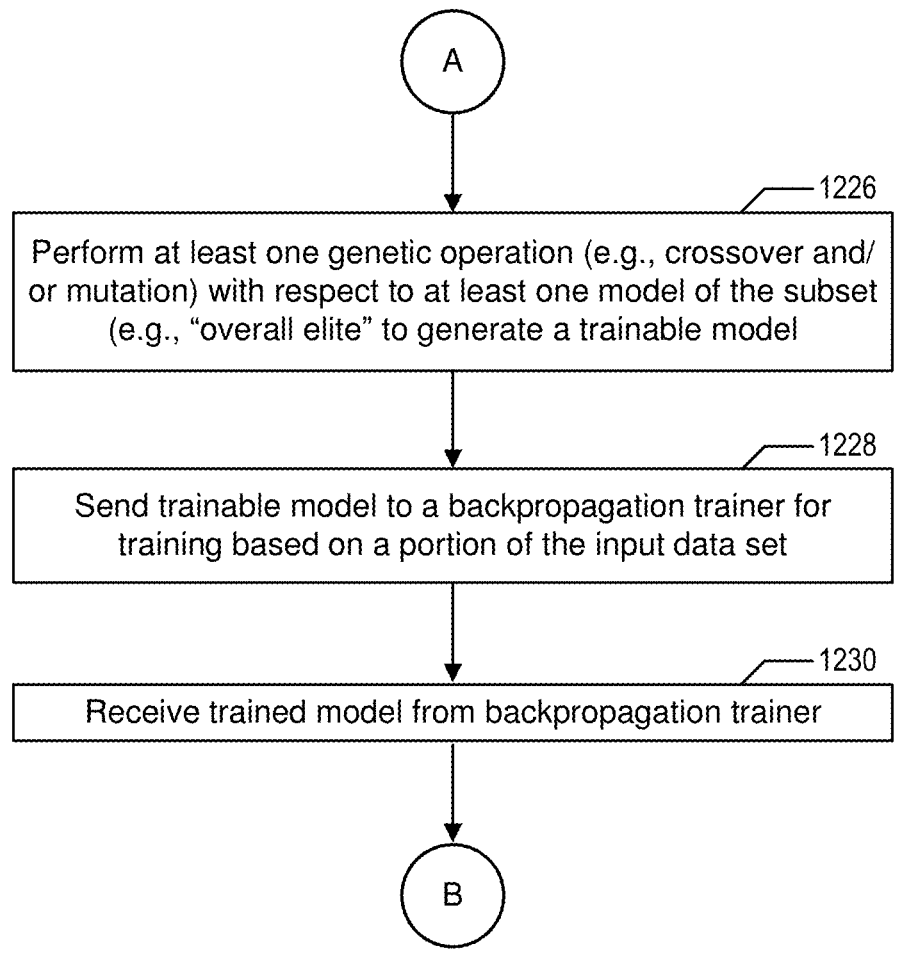

FIGS. 12A and 12B depict a particular example of a method 1200 of cooperative execution of a genetic algorithm and a backpropagation trainer. In an illustrative example, the method 1200 may be performed at the system 100 of FIG. 1.

The method 1200 may start, at 1202, and may include generating a randomized input population of models based on an input data set, at 1204. Each model may include data representative of a neural network. For example, each model may include at least node data and connection data, as described with reference to FIGS. 1 and 2. Further, each of the models may be part of the input set 120 of FIG. 1 and may model the input data set 102 of FIG. 1.

The method 1200 may also include determining, based on a fitness function, a fitness value of each model of the input population, at 1206. For example, the fitness of each model of the input set 120 may be determined, as described with reference to FIGS. 1 and 7.

The method 1200 may further include determining a subset of models based on their respective fitness values, at 1208. The subset of models may be the fittest models of the input population, e.g., "overall elites." For example, "overall elites" may be determined as described with reference to FIGS. 1 and 8.

The method 1200 may include performing multiple sets of operations at least partially concurrently. Continuing to 1226 (in FIG. 12B), the method 1200 may include performing at least one genetic operation with respect to at least one model of the subset to generate a trainable model. For example, the crossover operation 160 and/or the mutation operation 170 may be performed with respect to the "overall elites" to generate the trainable model 122, as described with reference to FIGS. 1, 8, and 9.

The method 1200 may also include sending the trainable model to a backpropagation trainer (or other optimization trainer) for training based on a portion of the input data set, at 1228. For example, the backpropagation trainer 180 of FIG. 1 may train the trainable model 122 based on a portion of the input data set 102 to generate the trained model 182, as described with reference to FIGS. 1 and 9.

The genetic algorithm may continue while backpropagation training occurs. For example, the method 1200 may include grouping the input population of models into species based on genetic distance, at 1210, and determining species fitness of each species, at 1212. To illustrate, the models of the input set 120 may be grouped into species and species fitness may be evaluated as described with reference to FIGS. 1, 7, and 8.

Continuing to 1214, species that satisfy a stagnation criteria may be removed. For example, species satisfying the stagnation criterion 150 may be removed, as described with reference to FIGS. 1 and 8. At 1216, the method 1200 may include identifying a subset of species based on their respective fitness values and identifying models of each species in the subset based on their respective model fitness values. The subset of species may be the fittest species of the input population, e.g., "elite species," and the identified models of the "elite species" may be the fittest members of those species, e.g., "elite members." For example, species fitness values, "elite species," and "elite members" may be determined as described with reference to FIGS. 1 and 8.

The method 1200 may include determining an output population that includes each "elite member," the "overall elites," and at least one model that is generated based on intra-species reproduction, at 1218. For example, the models of the output set 130 of FIG. 1 may be determined, where the output set 130 includes the overall elite models 860-864, the elite members (including the elite member model 870), and at least one model generated based on intra-species reproduction using the crossover operation 160 and/or the mutation operation 170, as described with reference to FIGS. 1 and 10.

The method 1200 may include determining whether a termination criterion is satisfied, at 1220. The termination criterion may include a time limit, a number of epochs, or a threshold fitness value of an overall fittest model, as illustrative non-limiting examples. If the termination criterion is not satisfied, the method 1200 returns to 1206 and a next epoch of the genetic algorithm is executed, where the output population determined at 1218 is the input population of the next epoch.

As described above, while the genetic algorithm is ongoing, the backpropagation trainer may train the trainable model to generate a trained model. When training is complete, the method 1200 may include receiving the trained model from the backpropagation trainer (or other optimization trainer), at 1230 (in FIG. 12B). The trained model may be added to the input set of an epoch of the genetic algorithm, as shown in FIG. 12B.

When the termination criterion is satisfied, at 1220, the method 1200 may include selecting and outputting a fittest model, at 1222, and the method 1200 may end, at 1224. In some implementations, the selected model may be subjected to a final training operation, e.g., by the backpropagation trainer or by another trainer, before being output.

Figure 13:
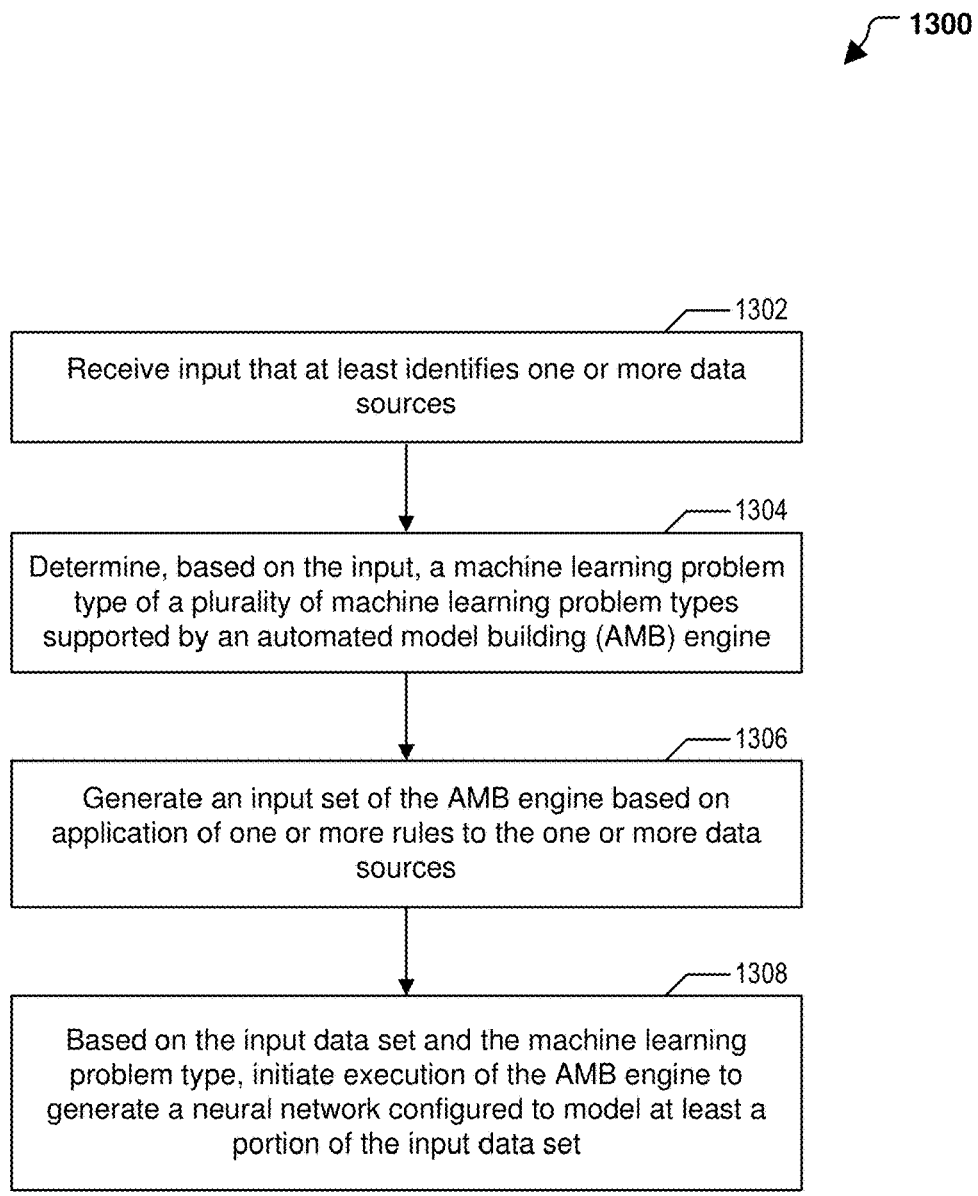
FIG. 13 illustrates a particular example of a method of operation at a pre-processor for data-driven model creation.

FIG. 13 depicts a particular example of a method 1300 of pre-processing for data-driven model creation. In an illustrative example, the method 1300 is performed at the pre-processor 104.

The method 1300 may include receiving input that identifies one or more data sources, at 1302. For example, the pre-processor 104 may receive input identifying one or more files, tables, a folder of files, etc. as described with reference to FIG. 3 and the GUIs of FIGS. 4-6. In some examples, the pre-processor 104 may combine portion(s) of the one or more data sources to determine a combined data source, as described with reference to FIG. 3.

The method 1300 may also include determining, based on the input, a machine learning problem type of a plurality of machine learning problem types supported by an AMB engine, at 1304. For example, the pre-processor 104 may determine a classification problem type if prediction target(s) include a categorical column, as described with reference to FIGS. 3 and 4. As another example, the pre-processor 104 may determine a regression problem type if prediction target(s) include a numerical column, as described with reference to FIGS. 3 and 5. As another example, the pre-processor 104 may determine a reinforcement learning problem type in response to receiving input indicating a state data structure, an action data structure, a reward function, an interaction function, etc.

The method 1300 may further include generating an input data set of the AMB engine based on application of one or more rules to the one or more data sources, at 1306. For example, the pre-processor 104 may generate the input data set 102 based on application of the rules 328. The rules 328 may include rules regarding identification of different column types, dropping of columns, one-hot encoding of categorical columns, etc.

The method 1300 may include, based on the input data set and the machine learning problem type, initiating execution of the AMB engine to generate a neural network configured to model at least a portion of the input data set, at 1308. For example, the pre-processor 104 may provide the input data set 102 to the genetic algorithm 110 and to the backpropagation trainer 180 along with one or more parameters and an indication of the machine learning problem type.

The AMB engine may then generate and train neural networks, for example in accordance with the method 1200 of FIG. 12. Thus, in particular aspects the method 1300 may be performed at the system 100 of FIG. 1 prior to the method 1200 of FIG. 12. To illustrate, the input data set generated in step 1308 of FIG. 13 may be used to generate the randomized input population of models at step 1204 of FIG. 12.

It is to be understood that the division and ordering of steps in FIGS. 12A, 12B, and 13 is for illustrative purposes only and is not be considered limiting. In alternative implementations, certain steps may be combined and other steps may be subdivided into multiple steps. Moreover, the ordering of steps may change. For example, the termination criterion may be evaluated after determining the "overall elites," at 1208, rather than after determining the output population, at 1218.

In conjunction with the described aspects, a computer system may include a memory configured to store an input data set and a plurality of data structures, each of the plurality of data structures including data representative of a neural network. The system also includes a processor configured to execute a recursive search. Executing the recursive search includes, during a first iteration: determining a fitness value for each of the plurality of data structures based on at least a subset of the input data set, selecting a subset of data structures from the plurality of data structures based on the fitness values of the subset of data structures, performing at least one of a crossover operation or a mutation operation with respect to at least one data structure of the subset to generate a trainable data structure, and providing the trainable data structure to an optimization trainer. The optimization trainer is configured to train the trainable data structure based on a portion of the input data set to generate a trained data structure and to provide the trained data structure as input to a second iteration of the recursive search that is subsequent to the first iteration.

In conjunction with the described aspects, a method includes, based on a fitness function, selecting, by a processor of a computing device, a subset of models from a plurality of models. The plurality of models is generated based on a genetic algorithm and corresponds to a first epoch of the genetic algorithm. Each of the plurality of models includes data representative of a neural network. The method also includes performing at least one genetic operation of the genetic algorithm with respect to at least one model of the subset to generate a trainable model and sending the trainable model to an optimization trainer. The method includes adding a trained model received from the optimization trainer as input to a second epoch of the genetic algorithm that is subsequent to the first epoch.

In conjunction with the described aspects, a computer-readable storage device stores instructions that, when executed, cause a computer to perform operations including, based on a fitness function, selecting a subset of models from a plurality of models. The plurality of models is generated based on a genetic algorithm and corresponds to a first epoch of the genetic algorithm. Each of the plurality of models includes data representative of a neural network. The operations also include performing at least one genetic operation of the genetic algorithm with respect to at least one model of the subset to generate a trainable model and sending the trainable model to a trainer. The operations include adding a trained model received from the trainer as input to a second epoch of the genetic algorithm that is subsequent to the first epoch.

In conjunction with the described aspects, a method includes receiving, at a processor of a computing device, input that identifies one or more data sources. The method also includes determining, based on the input, a machine learning problem type of a plurality of machine learning problem types supported by an AMB engine. The method further includes generating an input data set of the AMB engine based on application of one or more rules to the one or more data sources. The method includes, based on the input data set and the machine learning problem type, initiating execution of the AMB engine to generate a neural network configured to model at least a portion of the input data set.

In conjunction with the described aspects, a computer system includes an automated model building (AMB) pre-processor configured to receive input that identifies one or more data sources and to determine, based on the input, a machine learning problem type of a plurality of machine learning problem types supported by an AMB engine. The AMB pre-processor is also configured to generate an input data set of the AMB engine based on application of one or more rules to the one or more data sources. The AMB pre-processor is further configured to, based on the input data set and the machine learning problem type, initiate execution of the AMB engine to generate a neural network configured to model at least a portion of the input data set.

In conjunction with the described aspects, a computer-readable storage device stores instructions that, when executed, cause a computer to perform operations including receiving input that identifies one or more data sources. The operations also include determining, based on the input, a machine learning problem type of a plurality of machine learning problem types supported by an AMB engine and generating an input data set of the AMB engine based on application of one or more rules to the one or more data sources. The operations further include, based on the input data set and the machine learning problem type, initiating execution of the AMB engine to generate a neural network configured to model at least a portion of the input data set.

The systems and methods illustrated herein may be described in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, Java, JavaScript, VBScript, Macromedia Cold Fusion, COBOL, Microsoft Active Server Pages, assembly, PERL, PHP, AWK, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of techniques for data transmission, signaling, data processing, network control, and the like.

The systems and methods of the present disclosure may be embodied as a customization of an existing system, an add-on product, a processing apparatus executing upgraded software, a standalone system, a distributed system, a method, a data processing system, a device for data processing, and/or a computer program product. Accordingly, any portion of the system or a module may take the form of a processing apparatus executing code, an internet based (e.g., cloud computing) embodiment, an entirely hardware embodiment, or an embodiment combining aspects of the internet, software and hardware. Furthermore, the system may take the form of a computer program product on a computer-readable storage medium or device having computer-readable program code (e.g., instructions) embodied or stored in the storage medium or device. Any suitable computer-readable storage medium or device may be utilized, including hard disks, CD-ROM, optical storage devices, magnetic storage devices, and/or other storage media. A computer-readable storage medium or device is not a signal.

Systems and methods may be described herein with reference to screen shots, block diagrams and flowchart illustrations of methods, apparatuses (e.g., systems), and computer media according to various aspects. It will be understood that each functional block of a block diagrams and flowchart illustration, and combinations of functional blocks in block diagrams and flowchart illustrations, respectively, can be implemented by computer program instructions.

Computer program instructions may be loaded onto a computer or other programmable data processing apparatus to produce a machine, such that the instructions that execute on the computer or other programmable data processing apparatus create means for implementing the functions specified in the flowchart block or blocks. These computer program instructions may also be stored in a computer-readable memory or device that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions.

Although the disclosure may include a method, it is contemplated that it may be embodied as computer program instructions on a tangible computer-readable medium, such as a magnetic or optical memory or a magnetic or optical disk/disc. All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

Changes and modifications may be made to the disclosed embodiments without departing from the scope of the present disclosure. These and other changes or modifications are intended to be included within the scope of the present disclosure, as expressed in the following claims.

What is claimed is:

1. A method comprising:
receiving, at a processor of a computing device, input that identifies one or more data sources;
determining, based on the input, a machine learning problem type of a plurality of machine learning problem types supported by an automated model building (AMB) engine;
generating an input data set for the AMB engine including extracting first data values from the one or more data sources and modifying the first data values to generate second data values based on application of one or more rules, wherein the second data values include at least one value that is not present in the first data values; and
based on the input data set and the machine learning problem type, initiating execution of the AMB engine to generate a neural network configured to model at least a portion of the input data set.

2. The method of claim 1, wherein the input further comprises an indication of a constraint for generation of the neural network by the AMB engine.

3. The method of claim 2, wherein modifying the first data values to generate the second data values includes scaling the first data values.

4. The method of claim 1, further comprising generating a data profile including information regarding data fields of the one or more data sources, wherein the input data set is generated based on the data profile.

5. The method of claim 4, wherein generating the input data set further comprises omitting, from the input data set, one or more columns of data of the one or more data sources based on the data profile.

6. The method of claim 4, wherein the data profile of a particular column indicates a type of data stored in the particular column.

7. The method of claim 4, wherein the data profile of a particular column indicates a statistical metric descriptive of data stored in the particular column.

8. A computer system comprising:
an automated model building (AMB) pre-processor configured to:
receive input that identifies one or more data sources;
determine a machine learning problem type of a plurality of machine learning problem types supported by an AMB engine;
generate an input data set for the AMB engine including extracting first data values from the one or more data sources and modifying the first data values to generate second data values based on application of one or more rules, wherein the second data values include at least one value that is not present in the first data values; and
based on the input data set and the machine learning problem type, initiate execution of the AMB engine to generate a neural network configured to model at least a portion of the input data set.

9. The computer system of claim 8, wherein the AMB pre-processor comprises a data source analyzer configured to determine a combined data source based on the one or more data sources, wherein the combined data source is used to generate the input data set.

10. The computer system of claim 8, wherein the AMB pre-processor comprises a data profiler configured to determine a data profile including information regarding data fields of the one or more data sources, wherein the input data set is generated based on the data profile.

11. The computer system of claim 8, wherein the AMB pre-processor is further configured to determine, based on the machine learning problem type, an error function to be used by the AMB engine to evaluate one or more neural networks while generating the neural network configured to model at least the portion of the input data set.

12. The computer system of claim 8, wherein the AMB pre-processor is further configured to determine data sampling criteria used to generate the input data set to compensate for data imbalances in the one or more data sources.

13. The computer system of claim 8, wherein the AMB engine comprises a first device configured to execute a genetic algorithm.

14. The computer system of claim 13, wherein the AMB engine comprises a second device configured to execute an optimizer.

15. The computer system of claim 8, wherein the input further identifies one or more data fields of the input data set to be modeled by the AMB engine, and wherein the AMB pre-processor is configured to determine the machine learning problem type based at least in part on the one or more data fields of the input data set to be modeled.

16. The computer system of claim 8, wherein the input further identifies one or more parameters to control operation of the AMB engine, and wherein the AMB pre-processor is configured to initiate execution of the AMB engine based on the one or more parameters.

17. The computer system of claim 16, wherein the one or more parameters indicate one or more termination criteria for operation of the AMB engine, topology constraints for neural networks generated by the AMB engine, or both.

18. A computer-readable storage device storing instructions that, when executed, cause a computer to perform operations comprising:
receiving input that identifies one or more data sources;
determining, based on the input, a machine learning problem type of a plurality of machine learning problem types supported by an automated model building (AMB) engine;
generating an input data set for the AMB engine including extracting first data values from the one or more data sources and modifying the first data values to generate second data values based on application of one or more rules, wherein the second data values include at least one value that is not present in the first data values; and
based on the input data set and the machine learning problem type, initiating execution of the AMB engine to generate a neural network configured to model at least a portion of the input data set.

19. The computer-readable storage device of claim 18, wherein the operations include generating output to a display device, the output including one or more graphical user interfaces (GUIs) configured to receive the input.

20. The computer-readable storage device of claim 19, wherein one or more GUIs are configured to receive additional input indicating the machine learning problem type, one or more termination criteria for operation of the AMB engine, topology constraints for neural networks generated by the AMB engine, or a combination thereof.

* * * * *

UNITED STATES PATENT AND TRADEMARK OFFICE
CERTIFICATE OF CORRECTION

PATENT NO. : 11,687,786 B2
APPLICATION NO. : 17/002142
DATED : June 27, 2023
INVENTOR(S) : Sari Andoni, Keith D. Moore and Syed Mohammad Amir Husain It is certified that error appears in the above-identified patent and that said Letters Patent is hereby corrected as shown below:

In the Claims

Column 26, Claim 3, Line 18, after "claim" delete "2".
Column 26, Claim 3, Line 18, after "claim" insert --1--.

Signed and Sealed this
Eighth Day of August, 2023

Katherine Kelly Vidal
*Director of the United States Patent and Trademark Office*